US011338135B2

(12) United States Patent
Schmidt et al.

(10) Patent No.: US 11,338,135 B2
(45) Date of Patent: May 24, 2022

(54) MEDICAL DEVICES FOR CANCER THERAPY WITH ELECTRIC FIELD SHAPING ELEMENTS

(71) Applicant: Cardiac Pacemakers, Inc., St. Paul, MN (US)

(72) Inventors: Brian L. Schmidt, White Bear Lake, MN (US); Jacob M. Ludwig, Isanti, MN (US); Benjamin J. Haasl, Forest Lake, MN (US); Michael J. Kane, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/167,116

(22) Filed: Oct. 22, 2018

(65) Prior Publication Data

US 2019/0117972 A1 Apr. 25, 2019

Related U.S. Application Data

(60) Provisional application No. 62/575,700, filed on Oct. 23, 2017.

(51) Int. Cl.
*A61B 18/12* (2006.01)
*A61N 1/32* (2006.01)
(Continued)

(52) U.S. Cl.
CPC .......... *A61N 1/36002* (2017.08); *A61B 18/14* (2013.01); *A61B 18/18* (2013.01);
(Continued)

(58) Field of Classification Search
CPC ........................... A61N 1/36002; A61B 18/18
See application file for complete search history.

(56) References Cited

U.S. PATENT DOCUMENTS

| 4,016,886 A | 4/1977 | Doss et al. |
| 5,397,342 A | 3/1995 | Heil et al. |

(Continued)

FOREIGN PATENT DOCUMENTS

| AU | 2005301103 | 5/2006 |
| CN | 101693875 | 4/2010 |

(Continued)

OTHER PUBLICATIONS

International Search Report and Written Opinion for PCT Application No. PCT/US2018/057117 dated Dec. 20, 2018 (14 pages).

(Continued)

*Primary Examiner* — Unsu Jung
*Assistant Examiner* — Adreanne A. Arnold
(74) *Attorney, Agent, or Firm* — Pauly, DeVries Smith & Deffner LLC

(57) ABSTRACT

Embodiments herein relate to medical device systems including electric field shaping elements for use in treating cancerous tumors within a bodily tissue. In an embodiment, a medical device system for treating a cancerous tumor is described. The medical device system can include one or more electric field generating electrodes and an electric field shaping element configured to be implanted along with the one or more electric field generating electrodes. The electric field shaping element can be made from a material that alters the spatial area of tissue exposed to the electric field. Other embodiments are also included herein.

14 Claims, 12 Drawing Sheets

(51) Int. Cl.
*A61N 1/36* (2006.01)
*A61N 1/04* (2006.01)
*A61N 5/02* (2006.01)
*A61B 18/18* (2006.01)
*A61N 1/375* (2006.01)
*A61B 18/14* (2006.01)
*A61N 1/05* (2006.01)

(52) U.S. Cl.
CPC ......... *A61N 1/0492* (2013.01); *A61N 1/3756* (2013.01); *A61N 5/02* (2013.01); *A61N 1/0476* (2013.01); *A61N 1/0504* (2013.01)

(56) References Cited

U.S. PATENT DOCUMENTS

| | | | |
|---|---|---|---|
| 5,458,597 | A | 10/1995 | Edwards et al. |
| 5,582,609 | A | 12/1996 | Swanson et al. |
| 5,834,051 | A | 11/1998 | Woloszko et al. |
| 6,366,808 | B1 | 4/2002 | Schroeppel et al. |
| 6,673,623 | B1 | 1/2004 | Huberman |
| 6,868,289 | B2 | 3/2005 | Palti |
| 7,565,205 | B2 | 7/2009 | Palti |
| 7,656,205 | B2 | 2/2010 | Chen et al. |
| 7,715,921 | B2 | 5/2010 | Palti |
| 7,805,201 | B2 | 9/2010 | Palti |
| 7,809,441 | B2 | 10/2010 | Kane et al. |
| 7,890,183 | B2 | 2/2011 | Palti et al. |
| 7,917,227 | B2 | 3/2011 | Palti |
| 8,002,821 | B2 | 8/2011 | Stinson |
| 8,019,414 | B2 | 9/2011 | Palti |
| 8,170,648 | B2 | 5/2012 | Field et al. |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,500,713 | B2 | 8/2013 | Ferek-Petric |
| 8,706,261 | B2 | 4/2014 | Palti |
| 8,715,203 | B2 | 5/2014 | Palti |
| 8,718,756 | B2 | 5/2014 | Palti |
| 8,764,675 | B2 | 7/2014 | Palti |
| 9,023,090 | B2 | 5/2015 | Palti |
| 9,023,091 | B2 | 5/2015 | Palti |
| 9,039,674 | B2 | 5/2015 | Palti et al. |
| 9,056,203 | B2 | 6/2015 | Palti et al. |
| 9,248,278 | B2 | 2/2016 | Crosby et al. |
| 9,283,383 | B2 | 3/2016 | Osypka |
| 9,308,039 | B2 | 4/2016 | Azure |
| 9,440,068 | B2 | 9/2016 | Palti et al. |
| 9,630,022 | B2 | 4/2017 | Bourke et al. |
| 9,655,669 | B2 | 5/2017 | Palti et al. |
| 9,750,934 | B2 | 9/2017 | Palti et al. |
| 9,833,617 | B2 | 12/2017 | Travers et al. |
| 9,910,453 | B2 | 3/2018 | Wasserman et al. |
| 10,029,117 | B2 | 7/2018 | Bourke |
| 10,471,254 | B2 | 11/2019 | Sano et al. |
| 2002/0049485 | A1 | 4/2002 | Smits |
| 2003/0020416 | A1 | 1/2003 | Kobayashi |
| 2003/0069623 | A1 | 4/2003 | Stypulkowski |
| 2003/0204161 | A1* | 10/2003 | Ferek-Petric ............ A61N 1/40 604/20 |
| 2004/0010290 | A1 | 1/2004 | Schroeppel et al. |
| 2004/0158288 | A1 | 8/2004 | Keisari et al. |
| 2004/0176804 | A1 | 9/2004 | Palti |
| 2005/0004507 | A1 | 1/2005 | Schroeppel et al. |
| 2005/0096584 | A1 | 5/2005 | Ferek-petric |
| 2005/0209642 | A1 | 9/2005 | Palti |
| 2005/0222623 | A1 | 10/2005 | Kroll et al. |
| 2005/0222646 | A1 | 10/2005 | Kroll et al. |
| 2005/0240173 | A1 | 10/2005 | Palti |
| 2005/0288730 | A1 | 12/2005 | Deem et al. |
| 2006/0024802 | A1* | 2/2006 | Muller ............ B01L 3/502761 435/173.1 |
| 2006/0149341 | A1* | 7/2006 | Palti ...................... A61N 1/0408 607/63 |
| 2006/0282122 | A1* | 12/2006 | Palti ........................ A61N 1/40 607/2 |
| 2007/0033660 | A1 | 2/2007 | Palti |
| 2007/0225766 | A1 | 9/2007 | Palti |
| 2007/0239213 | A1* | 10/2007 | Palti ................... A61K 41/0052 607/3 |
| 2007/0239244 | A1 | 10/2007 | Morgan et al. |
| 2008/0086073 | A1 | 4/2008 | McDaniel |
| 2008/0275524 | A1 | 11/2008 | Furness et al. |
| 2009/0076500 | A1 | 3/2009 | Azure et al. |
| 2010/0016936 | A1 | 1/2010 | Stevenson et al. |
| 2010/0198298 | A1 | 8/2010 | Schulman et al. |
| 2010/0261994 | A1 | 10/2010 | Davalos et al. |
| 2010/0298895 | A1 | 11/2010 | Ghaffari et al. |
| 2010/0331938 | A1 | 12/2010 | Sommer et al. |
| 2011/0137229 | A1 | 6/2011 | Palti et al. |
| 2012/0035616 | A1 | 2/2012 | Olsen et al. |
| 2012/0203307 | A1 | 8/2012 | Schroeppel et al. |
| 2012/0283726 | A1 | 11/2012 | Palti |
| 2013/0165916 | A1 | 6/2013 | Mathur et al. |
| 2013/0204068 | A1 | 8/2013 | Gnanashanmugam et al. |
| 2013/0261711 | A1 | 10/2013 | Sivo |
| 2013/0289664 | A1 | 10/2013 | Johanek |
| 2013/0310898 | A1 | 11/2013 | Ollivier et al. |
| 2014/0005753 | A1 | 1/2014 | Carbunaru |
| 2014/0052227 | A1 | 2/2014 | Wahlstrand et al. |
| 2014/0107511 | A1 | 4/2014 | Banet et al. |
| 2014/0350653 | A1 | 11/2014 | Shiroff et al. |
| 2015/0134022 | A1 | 5/2015 | Lee et al. |
| 2015/0180161 | A1 | 6/2015 | Olson et al. |
| 2015/0320995 | A1 | 11/2015 | Nazareth et al. |
| 2016/0022986 | A1 | 1/2016 | Travers et al. |
| 2016/0029960 | A1 | 2/2016 | Toth et al. |
| 2016/0068598 | A1 | 3/2016 | Yan et al. |
| 2016/0128767 | A1 | 5/2016 | Azamian et al. |
| 2016/0129276 | A1* | 5/2016 | Fried ...................... A61N 2/006 600/12 |
| 2016/0250483 | A1 | 9/2016 | Klimovitch et al. |
| 2016/0331459 | A1 | 11/2016 | Townley et al. |
| 2016/0346536 | A1 | 12/2016 | Palti et al. |
| 2017/0007310 | A1 | 1/2017 | Rajagopalan et al. |
| 2017/0035496 | A1 | 2/2017 | Nagale et al. |
| 2017/0049514 | A1 | 2/2017 | Cosman |
| 2017/0105793 | A1 | 4/2017 | Cao et al. |
| 2017/0120041 | A1 | 5/2017 | Wenger et al. |
| 2017/0189098 | A1 | 7/2017 | Azure et al. |
| 2017/0215939 | A1 | 8/2017 | Palti et al. |
| 2017/0266371 | A1 | 9/2017 | Leonhardt et al. |
| 2017/0281934 | A1 | 10/2017 | Giladi et al. |
| 2017/0281955 | A1 | 10/2017 | Maile et al. |
| 2017/0312501 | A1 | 11/2017 | Bornzin et al. |
| 2018/0001075 | A1 | 1/2018 | Kirson et al. |
| 2018/0001078 | A1 | 1/2018 | Kirson et al. |
| 2018/0008708 | A1 | 1/2018 | Giladi et al. |
| 2018/0050200 | A1 | 2/2018 | Wasserman et al. |
| 2018/0110978 | A1 | 4/2018 | Beebe et al. |
| 2018/0154142 | A1 | 6/2018 | Guo et al. |
| 2018/0221088 | A1 | 8/2018 | Govari et al. |
| 2018/0246079 | A1 | 8/2018 | Wang et al. |
| 2018/0289954 | A1 | 10/2018 | Hebb et al. |
| 2019/0117969 | A1 | 4/2019 | Schmidt et al. |
| 2019/0117970 | A1 | 4/2019 | Schmidt et al. |
| 2019/0117971 | A1 | 4/2019 | Schmidt et al. |
| 2019/0117973 | A1 | 4/2019 | Schmidt et al. |
| 2020/0330756 | A1 | 10/2020 | Schmidt et al. |
| 2020/0330757 | A1 | 10/2020 | Schmidt et al. |
| 2020/0330758 | A1 | 10/2020 | Schmidt et al. |
| 2020/0338344 | A1 | 10/2020 | Schmidt et al. |
| 2020/0338345 | A1 | 10/2020 | Schmidt et al. |
| 2020/0338346 | A1 | 10/2020 | Schmidt et al. |
| 2021/0260370 | A1 | 8/2021 | Srivastava et al. |

(56) References Cited

U.S. PATENT DOCUMENTS

FOREIGN PATENT DOCUMENTS

| CN | 202365923 | 8/2012 |
|---|---|---|
| CN | 204698678 | 10/2015 |
| CN | 106823145 | 6/2017 |
| EP | 2942023 | 11/2015 |
| TW | 201039699 | 11/2010 |
| WO | 9513113 | 5/1995 |
| WO | 9526911 | 10/1995 |
| WO | 0158371 | 8/2001 |
| WO | 2009036457 | 3/2009 |
| WO | 2015100451 | 7/2015 |
| WO | 2016065263 | 4/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |

OTHER PUBLICATIONS

International Preliminary Report on Patentability for PCT Application No. PCT/US2018/057104 dated May 7, 2020 (8 pages).
International Preliminary Report on Patentability for PCT Application No. PCT/US2018/057115 dated May 7, 2020 (9 pages).
International Preliminary Report on Patentability for PCT Application No. PCT/US2018/057117 dated May 7, 2020 (8 pages).
International Preliminary Report on Patentability for PCT Application No. PCT/US2018/057120 dated May 7, 2020 (8 pages).
International Preliminary Report on Patentability for PCT Application No. PCT/US2018/057127 dated May 7, 2020 (8 pages).
Non-Final Office Action for U.S. Appl. No. 16/167,087 dated May 27, 2020 (31 pages).
Response to Non-Final Rejection dated Mar. 20, 2020 for U.S. Appl. No. 16/166,957, submitted via EFS-Web on Jun. 3, 2020, 16 pages.
International Search Report and Written Opinion for PCT Application No. PCT/US2018/057104 dated Dec. 20, 2018 (14 pages).
International Search Report and Written Opinion for PCT Application No. PCT/US2018/057115 dated Jan. 4, 2019 (13 pages).
International Search Report and Written Opinion for PCT Application No. PCT/US2018/057120 dated Dec. 19, 2018 (14 pages).
International Search Report and Written Opinion for PCT Application No. PCT/US2018/057127 dated Jan. 18, 2019 (12 pages).
Non-Final Office Action for U.S. Appl. No. 16/167,140 dated Apr. 6, 2020 (28 pages).
Non-Final Office Action for U.S. Appl. No. 16/166,957 dated Mar. 20, 2020 (44 pages).
Non-Final Office Action for U.S. Appl. No. 16/167,079 dated Apr. 17, 2020 (36 pages).
Final Office Action for U.S. Appl. No. 16/166,957 dated Jul. 21, 2020 (30 pages).
Final Office Action for U.S. Appl. No. 16/167,079 dated Sep. 15, 2020 (27 pages).
First Examination Report for Australian Patent Application No. 2018354149 dated Jul. 29, 2020 (5 pages).
First Examination Report for Australian Patent Application No. 2018354157 dated Jul. 31, 2020 (5 pages).
First Examination Report for Australian Patent Application No. 2018354159 dated Aug. 12, 2020 (5 pages).
Response to Non-Final Rejection dated Apr. 17, 2020 for U.S. Appl. No. 16/167,079, submitted via EFS-Web on Jul. 7, 2020, 17 pages.
Response to Non-Final Rejection dated Apr. 6, 2020 for U.S. Appl. No. 16/167,140, submitted via EFS-Web on Jul. 6, 2020, 12 pages.
Response to Non-Final Rejection dated May 27, 2020 for U.S. Appl. No. 16/167,087, submitted via EFS-Web on Aug. 20, 2020, 10 pages.
Di Sebastiano, Andrea R. et al., "Preclinical Outcomes of Intratumoral Modulation Therapy for Glioblastoma," Scientific Reports (2018) 8:7301 (11 pages).
Xu, Hu et al., "In Vitro Validation of Intratumoral Modulation Therapy for Glioblastoma," Anticancer Research 36:71-80 (2016), 10 pages.
Final Office Action for U.S. Appl. No. 16/167,087 dated Oct. 13, 2020 (21 pages).
First Examination Report for Australian Patent Application No. 2018354162 dated Sep. 29, 2020 (8 pages).
First Examination Report for Australian Patent Application No. 2018354167 dated Sep. 14, 2020 (5 pages).
Response to Final Rejection dated Jul. 21, 2020 for U.S. Appl. No. 16/166,957, submitted via EFS-Web on Oct. 13, 2020, 16 pages.
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
"Optune®—Elevate Expectations / Patient Information and Operation Manual," Novocure™, www.optune.com, 46, pages, Jan. 2019.
Final Office Action for U.S. Appl. No. 16/167,140 dated Oct. 19, 2020 (27 pages).
International Search Report and Written Opinion for PCT Application No. PCT/US2020/028508 dated Aug. 3, 2020 (13 pages).
International Search Report and Written Opinion for PCT Application No. PCT/US2020/028509 dated Jun. 30, 2020 (15 pages).
International Search Report and Written Opinion for PCT Application No. PCT/US2020/028512 dated Jul. 13, 2020 (14 pages).
International Search Report and Written Opinion for PCT Application No. PCT/US2020/029270 dated Oct. 26, 2020 (19 pages).
International Search Report and Written Opinion for PCT Application No. PCT/US2020/029274 dated Aug. 28, 2020 (19 pages).
International Search Report and Written Opinion for PCT Application No. PCT/US2020/029277 dated Jul. 13, 2020 (15 pages).
Invitation to Pay Additional Fees for PCT Application No. PCT/US2020/029270 dated Aug. 28, 2020 (14 pages).
Invitation to Pay Additional Fees for PCT Application No. PCT/US2020/029274 dated Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
Non-Final Office Action for U.S. Appl. No. 16/167,079 dated Jan. 6, 2021 (28 pages).
"Novocure Announces Launch of the inovitro™," Laboratory Research System, Press Release, 2 pages, Nov. 21, 2013, 2 pages.
Response to Communication Pursuant to Rules 161(1) and 162 EPC for European Patent Application No. 18800411.3 filed Dec. 9, 2020 (11 pages).
Response to Communication Pursuant to Rules 161(1) and 162 EPC for European Patent Application No. 18801134.0 filed Dec. 11, 2020 (9 pages).
Response to Communication Pursuant to Rules 161(1) and 162 EPC for European Patent Application No. 18801136.5 filed Dec. 10, 2020 (8 pages).
Response to Communication Pursuant to Rules 161(1) and 162 EPC for European Patent Application No. 18801137.3 filed Dec. 10, 2020 (7 pages).
Response to Communication Pursuant to Rules 161(1) and 162 EPC for European Patent Application No. 18801138.1 filed Dec. 11, 2020 (16 pages).
Response to Examination Report for Australian Patent Application No. 2018354149 filed Dec. 21, 2020 (14 pages).
Response to Examination Report for Australian Patent Application No. 2018354157 filed Dec. 31, 2020 (17 pages).
Response to Final Rejection dated Jul. 21, 2020 for U.S. Appl. No. 16/166,957, submitted via EFS-Web on Nov. 20, 2020, 21 pages.
Response to Final Rejection dated Sep. 15, 2020 for U.S. Appl. No. 16/167,079, submitted via EFS-Web on Nov. 5, 2020, 20 pages.
"Communication Pursuant to Article 94(3) EPC," for European Patent Application No. 18801138.1 dated Jun. 7, 2021 (7 pages).
"Examination Report," for Australian Patent Application No. 2018354162 dated Apr. 21, 2021 (5 pages).
"Final Office Action," for U.S. Appl. No. 16/166,957 dated May 14, 2021 (33 pages).
"Final Office Action," for U.S. Appl. No. 16/167,079 dated Jun. 23, 2021 (34 pages).

(56) References Cited

OTHER PUBLICATIONS

"First Office Action," for Chinese Patent Application No. 201880068896.3 dated Apr. 13, 2021 (17 pages) with English Summary.
"International Search Report and Written Opinion," for PCT Application No. PCT/US2021/019160 dated Jun. 2, 2021 (15 pages).
"Non-Final Office Action," for U.S. Appl. No. 16/167,087 dated Mar. 31, 2021 (28 pages).
"Non-Final Office Action," for U.S. Appl. No. 16/855,421 dated May 28, 2021 (37 pages).
"Office Action," for Canadian Patent Application No. 3,079,289 (our file dated May 28, 2021 (4 pages).
"Office Action," for Japanese Patent Application No. 2020-542719 dated Jun. 1, 2021 (9 pages) with English Translation.
"Response to Examination Report," for Australian Patent Application No. 2018354162 filed Mar. 30, 2021 (15 pages).
"Response to Non-Final Rejection," dated Jan. 6, 2021 for U.S. Appl. No. 16/267,079, submitted via EFS-Web on Apr. 6, 2021, 19 pages.
"Response to Non-Final Rejection," dated Mar. 31, 2021 for U.S. Appl. No. 16/167,087, submitted via EFS-Web on Jun. 23, 2021, 12 pages.
"Response to Second Examination Report," for Australian Patent Application No. 2018354149 filed Apr. 13, 2021 (19 pages).
"Office Action," for Japanese Patent Application No. 2020-542720 dated May 11, 2021 (13 pages) with English Translation.
"Communication Pursuant to Article 94(3) EPC," for European Patent Application No. 18801137.3 dated Mar. 5, 2021 (4 pages).
"Response to Non-Final Rejection," dated Feb. 17, 2021 for U.S. Appl. No. 16/166,957, submitted via EFS-Web on Mar. 17, 2021, 17 pages.
Examination Report for Australian Patent Application No. 2018354162 dated Feb. 4, 2021 (5 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
Non-Final Office Action for U.S. Appl. No. 16/166,957 dated Feb. 17, 2021 (37 pages).
Office Action for Japanese Patent Application No. 2020-542718 dated Feb. 9, 2021 (6 pages) No Translation.
Office Action for Japanese Patent Application No. 2020-542721 dated Feb. 9, 2021 (5 pages) No English Translation.
Office Action for Japanese Patent Application No. 2020-542722 dated Feb. 9, 2021 (5 pages) with English Summary.
Response to Examination Report for Australian Patent Application No. 2018354159 filed Jan. 18, 2021 (21 pages).
Response to Examination Report for Australian Patent Application No. 2018354162 filed Jan. 28, 2021 (15 pages).
Response to Examination Report for Australian Patent Application No. 2018354167 filed Jan. 28, 2021 (17 pages).
Response to Final Rejection dated Oct. 13, 2020 for U.S. Appl. No. 16/167,087, 11 pages, submitted via EFS-Web on Jan. 13, 2021.
Response to Final Rejection dated Oct. 19, 2020 for U.S. Appl. No. 16/167,140, submitted via EFS-Web on Jan. 19, 2021, 16 pages.
Second Examination Report for Australian Patent Application No. 2018354149 dated Jan. 8, 2021 (4 pages).
"Communication Pursuant to Article 94(3) EPC," for European Patent Application No. 18801137.3 dated Sep. 15, 2021 (4 pages).
"Decision of Rejection," for Japanese Patent Application No. 2020-542719 dated Oct. 19, 2021 (3 pages) No English Translation.
"First Office Action," for Chinese Patent Application No. 201880078117.8 dated Jul. 20, 2021 (14 pages) with English Summary.
"Non-Final Office Action," for U.S. Appl. No. 16/850,720 dated Aug. 24, 2021 (32 pages).
"Non-Final Office Action," for U.S. Appl. No. 16/855,433 dated Sep. 8, 2021 (32 pages).
"Office Action," for Japanese Patent Application No. 2020-542718 dated Oct. 19, 2021 (3 pages) No English Translation.
"Office Action," for Japanese Patent Application No. 2020-542722 dated Oct. 26, 2021 (5 pages) No English Translation.
"Response to Communication Pursuant to Article 94(3) EPC," for European Patent Application No. 18801138.1 filed Oct. 15, 2021 (10 pages).
"Response to Final Rejection dated," Aug. 2, 2021 for U.S. Appl. No. 16/167,087, submitted via EFS-Web on Nov. 1, 2021,12 pages.
"Response to Final Rejection," dated Jun. 23, 2021 and the Advisory Action dated Oct. 15, 2021 for U.S. Appl. No. 16/167,079, submitted via EFS-Web on Oct. 21, 2021, 19 pages.
"Response to Final Rejection," dated Jun. 23, 2021 for U.S. Appl. No. 16/167,079, submitted via EFS-Web on Sep. 9, 2021, 16 pages.
"Response to Final Rejection," dated May 14, 2021 and Advisory Action dated Aug. 26, 2021 for U.S. Appl. No. 16/166,957, submitted via EFS-Web on Sep. 10, 2021.
"Response to Non-Final Rejection," dated Aug. 24, 2021 for U.S. Appl. No. 16/850,720, submitted via EFS-Web on Nov. 1, 2021, 11 pages.
"Response to Non-Final Rejection," dated Jul. 12, 2021 for U.S. Appl. No. 16/167,140, submitted via EFS-Web on Oct. 12, 2021, 16 pages.
"Response to Non-Final Rejection," dated May 28, 2021 for U.S. Appl. No. 16/855,421, submitted via EFS-Web on Aug. 20, 2021, 11 pages.
"Response to Office Action," for Canadian Patent Application No. 3,079,289 filed with CIPO Sep. 23, 2021 (17 pages).
"Decision of Rejection," for Japanese Patent Application No. 2020-54219 dated Oct. 19, 2021 (6 pages) with English Translation.
"Final Office Action," for U.S. Appl. No. 16/850,720 dated Nov. 15, 2021 (15 pages).
"Final Office Action," for U.S. Appl. No. 16/855,421 dated Nov. 5, 2021 (25 pages).
"International Preliminary Report on Patentability," for PCT Application No. PCT/US2020/028508 dated Nov. 4, 2021 (8 pages).
"International Preliminary Report on Patentability," for PCT Application No. PCT/US2020/028509 dated Nov. 4, 2021 (9 pages).
"International Preliminary Report on Patentability," for PCT Application No. PCT/US2020/028512 dated Nov. 4, 2021 (8 pages).
"International Preliminary Report on Patentability," for PCT Application No. PCT/US2020/029270 dated Nov. 4, 2021 (11 pages).
"International Preliminary Report on Patentability," for PCT Application No. PCT/US2020/029274 dated Nov. 4, 2021 (13 pages).
"International Preliminary Report on Patentability," for PCT Application No. PCT/US2020/029277 dated Nov. 4, 2021 (10 pages).
"Non-Final Office Action," for U.S. Appl. No. 16/166,957 dated Dec. 22, 2021 (39 pages).
"Non-Final Office Action," for U.S. Appl. No. 16/167,087 dated Dec. 22, 2021 (24 pages).
"Office Action," for Canadian Patent Application No. 3,079,316 dated Oct. 27, 2021 (4 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Non-Final Rejection," dated Sep. 8, 2021 for U.S. Appl. No. 16/855,433, submitted via EFS-Web on Nov. 2, 2021, 12 pages.
"Response to Office Action," for Canadian Patent Application No. 3,079,314 filed Nov. 12, 2021 (14 pages).
"Second Office Action," for Chinese Patent Application No. 201880068896.3 dated Oct. 20, 2021 (6 pages), No English translation.
"Examination Report," for Canadian Patent Application No. 3,079,213 dated Jul. 12, 2021 (4 pages).
"Examination Report," for Canadian Patent Application No. 3,079,282 dated Jul. 14, 2021 (4 pages).
"Examination Report," for Canadian Patent Application No. 3,079,314 dated Jul. 14, 2021 (4 pages).
"Final Office Action," for U.S. Appl. No. 16/167,087 dated Aug. 2, 2021 (25 pages).
"Non-Final Office Action," for U.S. Appl. No. 16/167,140 dated Jul. 12, 2021 (32 pages).

(56) References Cited

OTHER PUBLICATIONS

"Response to Examination Report," for Australian Patent Application No. 2018354162 filed Jul. 13, 2021 (18 pages).
"Response to Final Rejection," dated May 14, 2021 for U.S. Appl. No. 16/166,957, submitted via EFS-Web on Aug. 5, 2021, 18 pages.

* cited by examiner

MEDICAL DEVICES FOR CANCER THERAPY WITH ELECTRIC FIELD SHAPING ELEMENTS

This application claims the benefit of U.S. Provisional Application No. 62/575,700, filed Oct. 23, 2017, the content of which is herein incorporated by reference in its entirety.

FIELD

Embodiments herein relate to medical device systems including electric field shaping elements for use in treating cancerous tumors within a bodily tissue. More specifically, embodiments herein relate to using electric field shaping elements configured to redirect or concentrate therapeutic electric fields at the site of a cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

Mitosis is the process of cellular division that is a part of the cell cycle for all somatic cells in the body, including many types of cancerous cells. Mitosis includes four basic phases: prophase, metaphase, anaphase, and telophase. Just prior to prophase, a cell will copy its chromosomes to create two identical sister chromatids. During prophase, the chromosomes start to condense and the nuclear membrane surrounding the nucleus disappears. The mitotic spindle also begins to form during prophase. The mitotic spindle includes a self-organized bipolar array of microtubules and centrosomes. Microtubules are generally formed from the polymerization of the highly polar alpha-tubulin and beta-tubulin proteins. Centrosomes are similarly protein-based organelles, two of which migrate to opposite sides of the dividing cell at this phase. The negatively charged end of the microtubules attach to the centrosomes. The positively charged end of the microtubules radiate toward the equator of the dividing cell where they eventually attach to a kinetochore of each sister chromatid. Metaphase can be defined by all chromosomes being aligned at the equator of the dividing cell and bound in the mitotic spindle. An equal number of sister chromatids are then pulled toward opposite ends of the cell during anaphase. Once all chromosomes have been separated, the process of telophase begins, where the cell membrane begins to form a cleavage furrow between the two newly forming sister cells, and cell division becomes complete once the cells physically separate from one another in a process called cytokinesis.

SUMMARY

Embodiments herein relate to medical device systems including electric field shaping elements for use in treating cancerous tumors within a bodily tissue. In a first aspect, a medical device system for treating a cancerous tumor is provided. The medical device system can include one or more electric field generating electrodes and an electric field shaping element configured to be implanted along with the one or more electric field generating electrodes. The electric field shaping element can be made from a material that alters the spatial area of tissue exposed to the electric field.

In a second aspect, in addition to one or more of the preceding or following aspects, or in the alternative to some aspects, the medical device can include a lead having the one or more electric field generating electrodes are disposed on the lead.

In a third aspect, in addition to one or more of the preceding or following aspects, or in the alternative to some aspects, the lead can include a lead body having a proximal end and a distal end. The lead body can include one or more conductors passing through the lead body to provide electrical communication between the one or more electric field generating electrodes and the proximal end of the lead body.

In a fourth aspect, in addition to one or more of the preceding or following aspects, or in the alternative to some aspects, the electric field shaping element can be physically separated from the lead and the one or more electric field generating electrodes.

In a fifth aspect, in addition to one or more of the preceding or following aspects, or in the alternative to some aspects, the electric field shaping element can include a material that shields an electrical field.

In a sixth aspect, in addition to one or more of the preceding or following aspects, or in the alternative to some aspects, the electric field shaping element can be disposed between a cancerous tumor and an adjacent non-cancerous tissue.

In a seventh aspect, in addition to one or more of the preceding or following aspects, or in the alternative to some aspects, the electric field shaping element can be disposed between an adjacent non-cancerous tissue and the one or more electric field generating electrodes.

In an eighth aspect, in addition to one or more of the preceding or following aspects, or in the alternative to some aspects, the electric field shaping element can include a material that redirects an electrical field.

In a ninth aspect, in addition to one or more of the preceding or following aspects, or in the alternative to some aspects, the electric field shaping element can include a material that attenuates the energy of an electrical field.

In a tenth aspect, in addition to one or more of the preceding or following aspects, or in the alternative to some aspects, the electric field shaping element can include a high-dielectric material.

In an eleventh aspect, in addition to one or more of the preceding or following aspects, or in the alternative to some aspects, the electric field shaping element can include a concave shape with respect to the cancerous tumor.

In a twelfth aspect, in addition to one or more of the preceding or following aspects, or in the alternative to some aspects, the electric field shaping element can include a parabolic shape with respect to the cancerous tumor.

In a thirteenth aspect, in addition to one or more of the preceding or following aspects, or in the alternative to some aspects, the electric field shaping element can be a polymer sheet.

In a fourteenth aspect, in addition to one or more of the preceding or following aspects, or in the alternative to some aspects, the polymer sheet can include one or more apertures disposed therein to focus an electric field onto a cancerous tumor.

In a fifteenth aspect, in addition to one or more of the preceding or following aspects, or in the alternative to some aspects, the electric field shaping element can be a metal sheet.

In a sixteenth aspect, in addition to one or more of the preceding or following aspects, or in the alternative to some aspects, the metal sheet can include one or more apertures disposed therein to focus an electric field onto a cancerous tumor.

In a seventeenth aspect, in addition to one or more of the preceding or following aspects, or in the alternative to some aspects, a medical device system for treating a cancerous tumor is provided. The medical device system can include one or more electric field generating electrodes and an electric field shaping element configured to be implanted along with the one or more field generating electrodes. The electric field shaping element can be configured to shield a non-cancerous tissue from an electric field.

In an eighteenth aspect, in addition to one or more of the preceding or following aspects, or in the alternative to some aspects, a lead is included, where the one or more field generating electrodes are disposed on the lead.

In a nineteenth aspect, in addition to one or more of the preceding or following aspects, or in the alternative to some aspects, the lead can include a lead body having a proximal end and a distal end. The lead body can include one or more conductors passing through the lead body to provide electrical communication between the one or more electrodes and the proximal end of the lead body.

In a twentieth aspect, in addition to one or more of the preceding or following aspects, or in the alternative to some aspects, the electric field shaping element can be physically separated from the lead and one or more electric field generating electrodes.

In a twenty-first aspect, in addition to one or more of the preceding or following aspects, or in the alternative to some aspects, the electric field shaping element can include a material that redirects an electrical field.

In a twenty-second aspect, in addition to one or more of the preceding or following aspects, or in the alternative to some aspects, the electric field shaping element can be a contiguous metal sheet.

In a twenty-third aspect, in addition to one or more of the preceding or following aspects, or in the alternative to some aspects, the contiguous metal sheet can include one or more apertures disposed therein to effectively shunt an electric field at an exterior surface of the metal sheet to prevent the electric field from contacting the non-cancerous tissue.

In a twenty-fourth aspect, in addition to one or more of the preceding or following aspects, or in the alternative to some aspects, the contiguous metal sheet can include an expandable lattice.

In a twenty-fifth aspect, in addition to one or more of the preceding or following aspects, or in the alternative to some aspects, a method of treating a cancerous tumor is provided. The method can include placing a material proximal to a cancerous tumor, wherein the material attenuates an electrical field less than the patient tissue being replaced, placing one or more electrodes on the opposite side of the material from the cancerous tumor, and generating an electric field at the site of the cancerous tumor from the one or more electrodes.

In a twenty-sixth aspect, in addition to one or more of the preceding or following aspects, or in the alternative to some aspects, placing the material comprises replacing a segment of a patient tissue with the material that attenuates the electric field less than the patient tissue being replaced.

In a twenty-seventh aspect, in addition to one or more of the preceding or following aspects, or in the alternative to some aspects, the material can include a natural material.

In a twenty-eighth aspect, in addition to one or more of the preceding or following aspects, or in the alternative to some aspects, the material can include a synthetic material.

In a twenty-ninth aspect, in addition to one or more of the preceding or following aspects, or in the alternative to some aspects, the method can include generating an electric field at the site of the cancerous tumor includes generating the electric field external to a patient's body.

In a thirtieth aspect, in addition to one or more of the preceding or following aspects, or in the alternative to some aspects, a medical device system for treating a cancerous tumor is included. The medical device can include one or more implanted electric field generating electrodes and an external electric field generating system configured to be coupled to the one or more implanted electric field generating electrodes to deliver an electric field to the site of the cancerous tumor.

In a thirty-first aspect, in addition to one or more of the preceding or following aspects, or in the alternative to some aspects, one or more implanted electric field generating electrodes and an external electric field generating system are wirelessly coupled through at least one mechanism selected from capacitive coupling, inductive coupling, conductive coupling, radio frequency energy transfer, and acoustic energy transfer.

In a thirty-second aspect, in addition to one or more of the preceding or following aspects, or in the alternative to some aspects, a system can also include an electric field shaping element configured to be implanted along with the one or more electric field generating electrodes.

In a thirty-third aspect, in addition to one or more of the preceding or following aspects, or in the alternative to some aspects, a method of treating a cancerous tumor is provided. The method can include placing an electric field shaping element proximal to a cancerous tumor. The method can also include placing one or more electrodes at, near, or within a cancerous tumor. The method can also include generating an electric field at the site of the cancerous tumor from the one or more electrodes.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
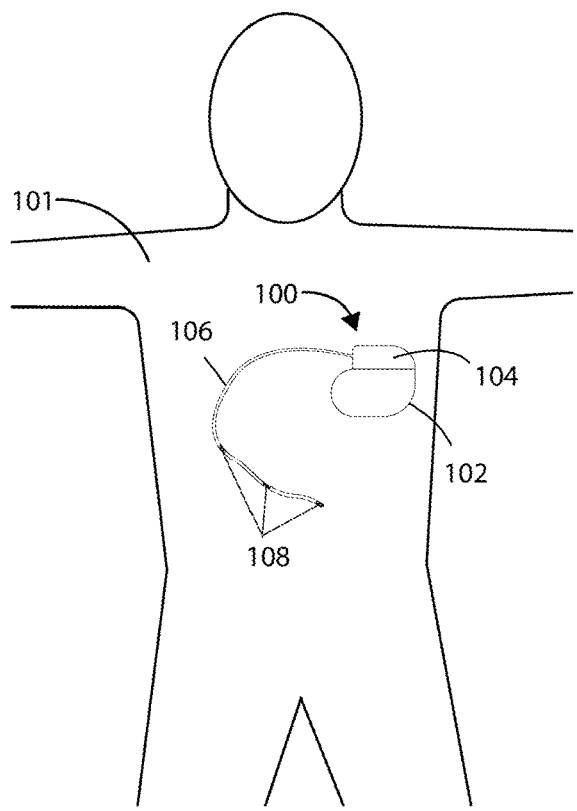
FIG. 1 is a schematic view of a medical system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that alternating electric fields can disrupt mitosis within a cancerous tumor by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an alternating electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death).

It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

The shape and size of an electric field can be modulated by the positioning of electrodes in space and by varying the electric field at a number of different electrode configurations. Sometimes, the shape of an electric field can be manipulated by alternating or switching the polarity of discrete electrodes within an individual array of electrodes or within the entire medical device system.

An electric field can also be manipulated by positioning electric field shaping elements at or near the site of treatment for a cancerous tumor. Electric field shaping elements can be configured to redirect an electric field such that it does not affect, or has a reduced effect upon, cells within an adjacent non-cancerous tissue. Electric field shaping elements can also be used to concentrate an electric field at the site of a cancerous tumor.

Referring now to FIG. 1, a schematic view is shown of a medical device 100 in accordance with various embodiments herein. The medical device 100 can be implanted entirely within the body of a patient 101 at or near the site of a cancerous tumor located within a bodily tissue. Various implant sites can be used including areas such as in the limbs, the upper torso, the abdominal area, the head, and the like.

Figure 2:
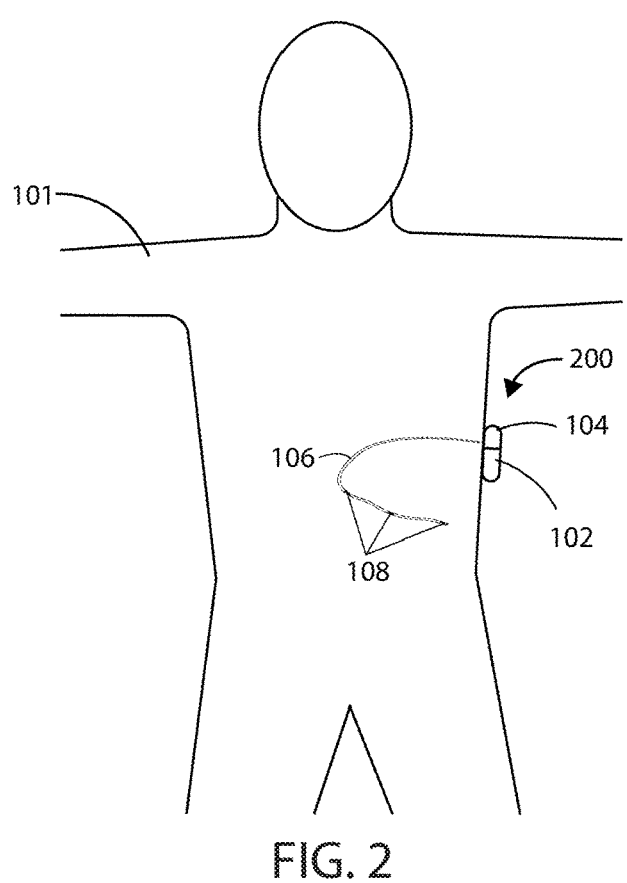
FIG. 2 is a schematic view of a medical system in accordance with various embodiments herein.

Referring now to FIG. 2, another schematic view is shown of a medical device 200 in accordance with various embodiments herein. The medical device 200 can be partially implanted within the body of a patient 101. In some embodiments, the medical device can be partially implanted and partially external to the body of a patient. In other embodiments, a partially implanted medical device can include a transcutaneous connection between components disposed internal to the body and external to the body. A partially implanted medical device can wirelessly communicate with a partially external portion of a medical device over a wireless connection.

In some embodiments, a portion of the medical device can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include the many of the same components as and can be configured to perform many of the same functions as a pulse generator. In embodiments where a portion of a medical device is entirely implanted and a portion of the medical device is entirely external, the portion of the medical device that is entirely external can communicate wirelessly with the portion of the medical device that is entirely internal. However, in other embodiments a wired connection can be used.

The medical device 100 or medical device 200 can include a housing 102 and a header 104 coupled to the housing 102. Various materials can be used. However, in some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of the medical device 100 or 200 is partially external, the header 104 and housing 102 can be surrounded by a protective casing made of a combination of polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. It will be appreciated that while many embodiments of medical devices herein are designed to function with leads, leadless medical devices that generate electrical fields are also contemplated herein.

Figure 3:
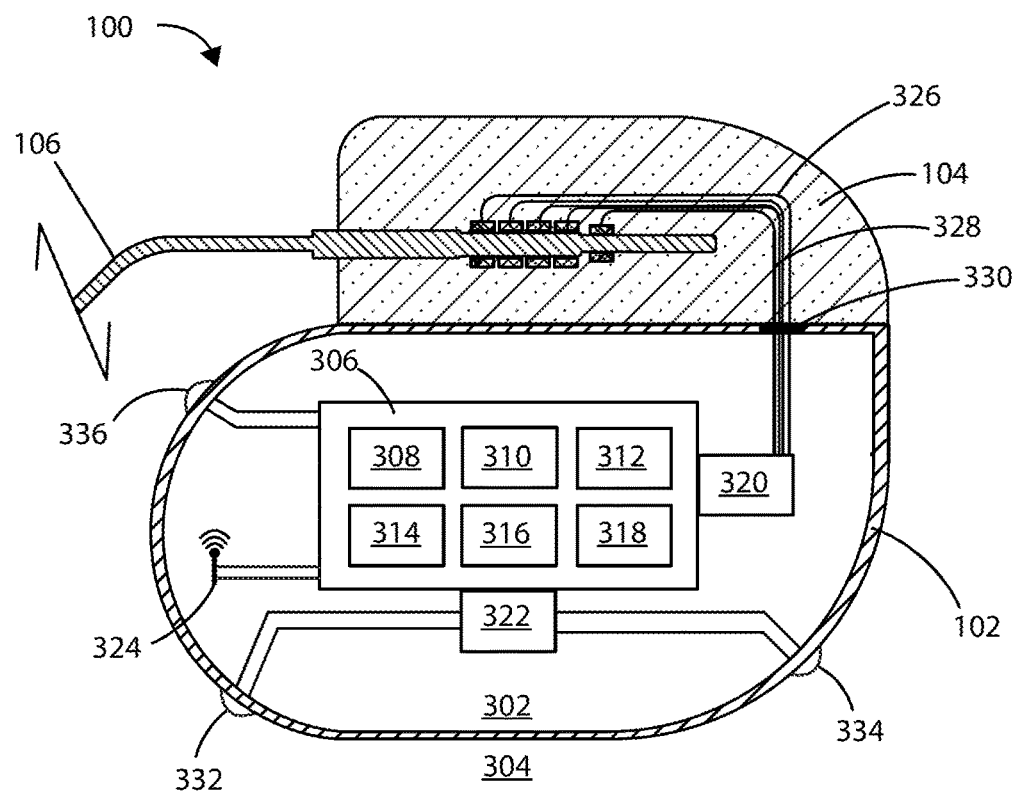
FIG. 3 is a schematic cross-sectional view of a medical device in accordance with various embodiments herein.

Referring now to FIG. 3, a schematic cross-sectional view of medical device 100 is shown in accordance with various embodiments herein. Housing 102 can define an interior volume 302 that can be hollow and that in some embodiments is hermetically sealed off from the area 304 outside of medical device 100. In other embodiments the housing 102 can be filled with components and/or structural materials such that it is non-hollow. The medical device 100 can include control circuitry 306, which can include various components 308, 310, 312, 314, 316, and 318 disposed within housing 102. In some embodiments, these components can be integrated and in other embodiments these components can be separate. In yet other embodiments, there can be a combination of both integrated and separate components. The medical device 100 can also include an antenna 324, to allow for unidirectional or bidirectional wireless data communication. In some embodiments, the components of medical device 100 can include an inductive energy receiver coil (not shown) communicatively coupled or attached thereto to facilitate transcutaneous recharging of the medical device via recharging circuitry.

The various components 308, 310, 312, 314, 316, and 318 of control circuitry 306 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 306 can be in communication with an electric field generating circuit 320 that can be configured to generate electric current to create one or more fields. The electric field generating circuit 320 can be integrated with the control circuitry 306 or can be a separate component from control circuitry 306. Control circuitry 306 can be configured to control delivery of electric current from the electric field generating circuit 320. In some embodiments, the electric field generating circuit 320 can be present in a portion of the medical device that is external to the body.

In some embodiments, the control circuitry 306 can be configured to direct the electric field generating circuit 320 to deliver an electric field using one or more frequencies selected from a range of between 10 kHz to 1 MHz. In some embodiments, the control circuitry 306 can be configured to direct the electric field generating circuit 320 to deliver an electric field at one or more frequencies selected from a range of between 100 kHz to 500 kHz. In some embodiments, the control circuitry 306 can be configured to direct the electric field generating circuit 320 to deliver an electric field at one or more frequencies selected from a range of between 100 kHz to 300 kHz. In some embodiments, the control circuitry 306 can be configured to direct the electric field generating circuit 320 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 306 can be configured to direct the electric field generating circuit 320 to deliver an electric field using currents ranging from 1 mAmp to 1000 mAmp to the site of a cancerous tumor. In some embodiments, the control circuitry 306 can be configured to direct the electric field generating circuit 320 to deliver an electric field using currents ranging from 20 mAmp to 500 mAmp to the site of a cancerous tumor. In some embodiments, the control circuitry 306 can be configured to direct the electric field generating circuit 320 to deliver an electric field using currents ranging from 30 mAmp to 300 mAmp to the site of a cancerous tumor.

In some embodiments, the control circuitry 306 can be configured to direct the electric field generating circuit 320 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 320 to deliver an electric field at a current falling within a range, wherein any of the forgoing currents can serve as the lower or upper bound of the range, provided that the lower bound of the range is a value less than the upper bound of the range.

In some embodiments, the control circuitry 306 can be configured to direct the electric field generating circuit 320 to deliver an electric field using voltages ranging from 1 $V_{rms}$ to 50 $V_{rms}$ to the site of a cancerous tumor. In some embodiments, the control circuitry 306 can be configured to direct the electric field generating circuit 320 to deliver an electric field using voltages ranging from 5 $V_{rms}$ to 30 $V_{rms}$ to the site of a cancerous tumor. In some embodiments, the control circuitry 306 can be configured to direct the electric field generating circuit 320 to deliver an electric field using voltages ranging from 10 $V_{rms}$ to 20 $V_{rms}$ to the site of a cancerous tumor.

In some embodiments, the control circuitry 306 can be configured to direct the electric field generating circuit 320 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit 320 to deliver an electric field using a voltage falling within a range, wherein any of the forgoing voltages can serve as the lower or upper bound of the range, provided that the lower bound of the range is a value less than the upper bound of the range.

In some embodiments, the control circuitry 306 can be configured to direct the electric field generating circuit 320 to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 320 can deliver an electric field using a frequency falling within a range, wherein any of the foregoing frequencies can serve as the upper or lower bound of the range, provided that the upper bound is greater than the lower bound.

In some embodiments, the control circuitry 306 can be configured to direct the electric field generating circuit 320 to generate one or more applied electric field strengths selected from a range of between 0.25 V/cm to 1000 V/cm. In some embodiments, the control circuitry 306 can be configured to direct the electric field generating circuit 320 to generate one or more applied electric field strengths of greater than 3 V/cm. In some embodiments, the control circuitry 306 can be configured to direct the electric field generating circuit 320 to generate one or more applied electric field strengths selected from a range of between 1 V/cm to 10 V/cm. In some embodiments, the control circuitry 306 can be configured to direct the electric field generating circuit 320 to generate one or more applied electric field strengths selected from a range of between 3 V/cm to 5 V/cm.

In other embodiments, the control circuitry 306 can be configured to direct the electric field generating circuit 320 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 320 can generate an electric field having a field strength at a treatment site falling within a range, wherein any of the foregoing field strengths can serve as the upper or lower bound of the range, provided that the upper bound is greater than the lower bound.

In some embodiments, the control circuitry 306 can be configured to direct the electric field generating circuit 320 to deliver an electric field via leads 106 to the site of a cancerous tumor located within a bodily tissue. In other embodiments, the control circuitry 306 can be configured to direct the electric field generating circuit 320 to deliver an electric field via the housing 102 of medical device 100 to the site of a cancerous tumor located within a bodily tissue. In other embodiments, the control circuitry 306 can be configured to direct the electric field generating circuit 320 to deliver an electric field between leads 106 and the housing 102 of medical device 100. In some embodiments, one or more leads 106 can be in electrical communication with the electric field generating circuit 320. In some embodiments, the one or more leads 106 can include one or more electrodes 108 disposed along the length of the leads 106, where the electrodes 108 can be in electrical communication with the electric field generating circuit 320.

In some embodiments, various components within medical device 100 can include an electric field sensing circuit 322 configured to generate a signal corresponding to sensed electric fields. Electric field sensing circuit 322 can be integrated with control circuitry 306 or it can be separate from control circuitry 306.

Sensing electrodes can be disposed on or adjacent to the housing of the medical device, on one or more leads connected to the housing, on a separate device implanted near or in the tumor, or any combination of these locations. In some embodiments, the electric field sensing circuit 322 can include a first sensing electrode 332 and a second sensing electrode 334. In other embodiments, the housing 102 itself can serve as a sensing electrode for the electric field sensing circuit 322. The electrodes 332 and 334 can be in communication with the electric field sensing circuit 322. The electric field sensing circuit 322 can measure the electrical potential difference (voltage) between the first electrode 332 and the second electrode 334. In some embodiments, the electric field sensing circuit 322 can measure the electrical potential difference (voltage) between the first electrode 332 or second electrode 334, and an electrode disposed along the length of one or more leads 106. In some embodiments, the electric field sensing circuit can be configured to measure sensed electric fields and to record electric field strength in V/cm.

It will be appreciated that the electric field sensing circuit 322 can additionally measure an electrical potential difference between the first electrode 332 or the second electrode 334 and the housing 102 itself. In other embodiments, the medical device can include a third electrode 336, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 320. The one or more leads 106 can include one or more electrodes 108, as shown in FIGS. 1 and 2. In some embodiments, various electrical conductors, such as electrical conductors 326 and 328, can pass from the header 104 through a feed-through structure 330 and into the interior volume 302 of medical device 100. As such, the electrical conductors 326 and 328 can serve to provide electrical communication between the one or more leads 106 and control circuitry 306 disposed within the interior volume 302 of the housing 102.

In some embodiments, recorder circuitry can be configured to record the data produced by the electric field sensing circuit 322 and record time stamps regarding the same. In some embodiments, the control circuitry 306 can be hardwired to execute various functions, while in other embodiments the control circuitry 306 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 4:
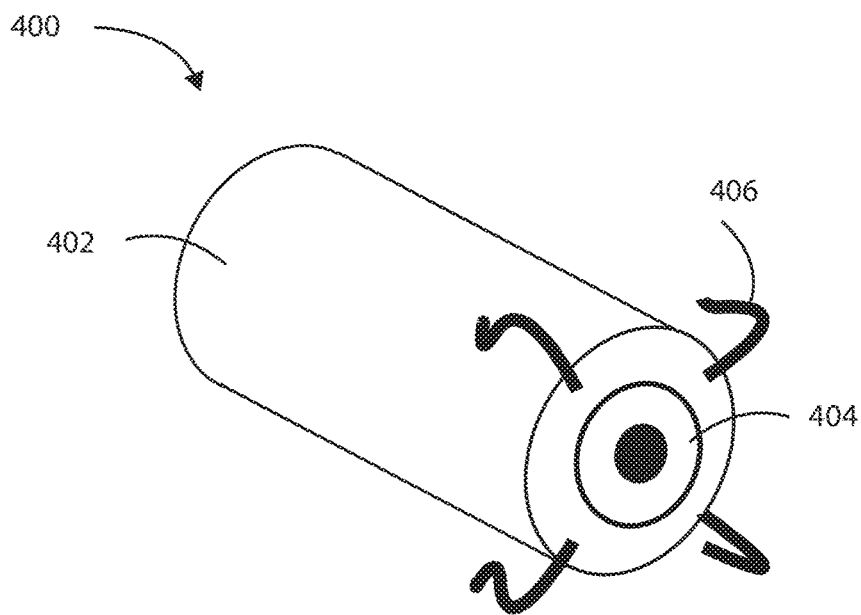
FIG. 4 is a schematic view of a medical device in accordance with various embodiments herein.

Referring now to FIG. 4, leadless medical device 400 is shown in accordance with the embodiments herein. The leadless medical device 400 can include a housing 402 and a header 404 coupled to the housing 402. Various materials can be used. However, in some embodiments, the housing 402 can be formed of a material such as a metal, ceramic, polymer, composite, or the like. In some embodiments, the housing 402, or one or more portions thereof, can be formed of titanium. The header 404 can be formed of various materials, but in some embodiments the header 404 can be formed of a translucent polymer such as an epoxy material. In some embodiments the header 404 can be hollow. In other embodiments the header 404 can be filled with components and/or structural materials such as epoxy or another material such that it is non-hollow. In some embodiments, leadless medical device 400 can include fixation elements 406 to keep a leadless medical device 400 positioned at or near the site of a cancerous tumor within the body. In some embodiments, fixation elements 406 can include talons, tines, helices, bias, and the like.

Figure 5:
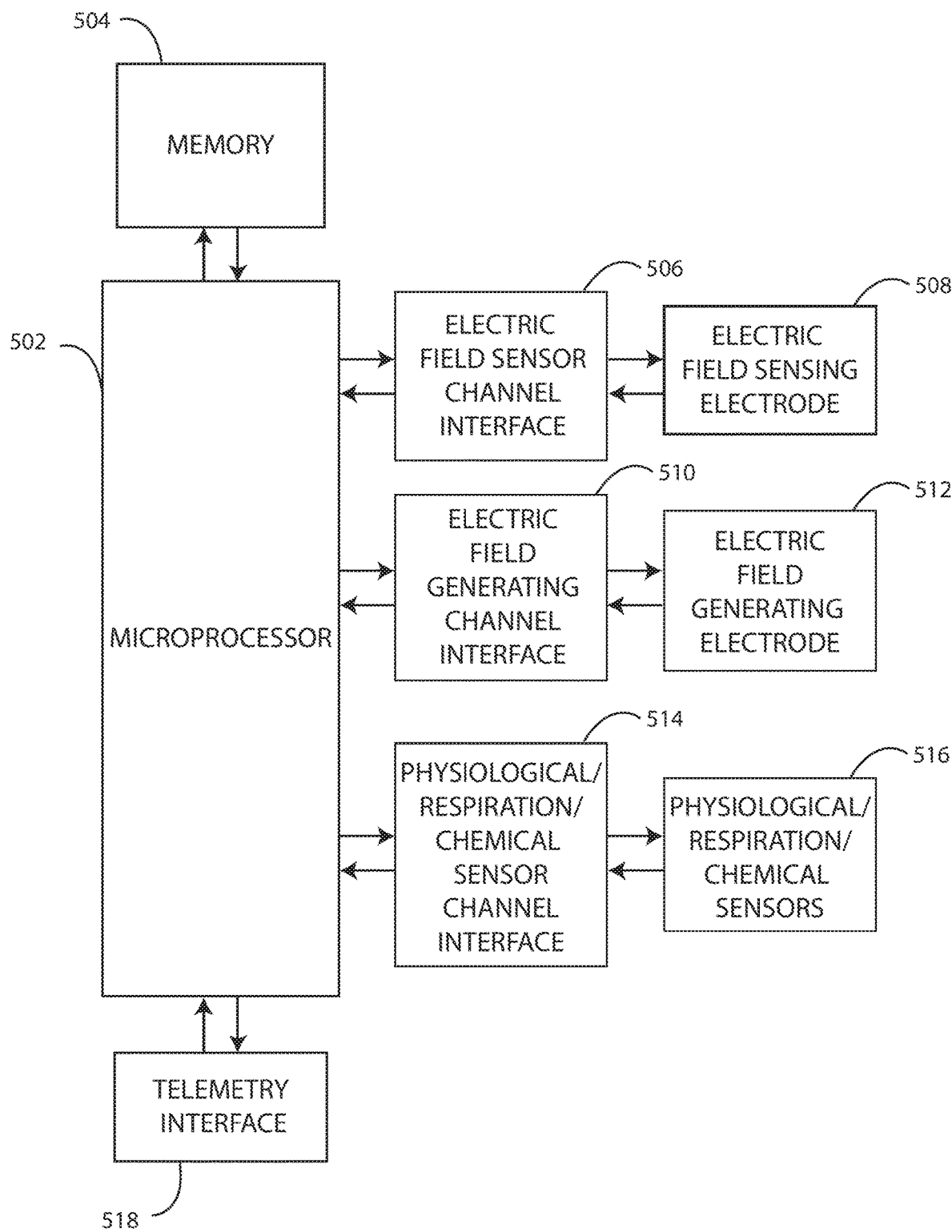
FIG. 5 is a schematic diagram of components of a medical device in accordance with various embodiments herein.

Elements of various embodiments of the medical devices described herein are shown in FIG. 5. However, it will be appreciated that some embodiments can include additional elements beyond those shown in FIG. 5. In addition, some embodiments may lack some elements shown in FIG. 5. The medical devices as embodied herein can gather information through one or more sensing channels and can output information through one or more field generating channels. A microprocessor 502 can communicate with a memory 504 via a bidirectional data bus. The memory 504 can include read only memory (ROM) or random access memory (RAM) for program storage and RAM for data storage. The microprocessor 502 can also be connected to a telemetry interface 518 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device.

The medical device can include one or more electric field sensing electrodes 508 and one or more electric field sensor channel interfaces 506 that can communicate with a port of microprocessor 502. The medical device can also include one or more electric field generating electrodes 512 and one or more electric field generating channel interfaces 510 that can communicate with a port of microprocessor 502. The medical device can also include one or more physiological sensors, respiration sensors, or chemical sensors 516 and one or more physiological/respiration/chemical sensor channel interfaces 514 that can communicate with a port of microprocessor 502. The channel interfaces 506, 510, and 514 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the physiological, respiration, or chemical sensors 516 are shown as part of a medical device in FIG. 5, it is realized that in some embodiments one or more of the physiological, respiration, or chemical sensors could be physically separate from the medical device. In various embodiments, one or more of the physiological, respiration, or chemical sensors can be within another implanted medical device communicatively coupled to a medical device via telemetry interface 518. In yet other embodiments, one or more of the physiological, respiration, or chemical sensors can be external to the body and coupled to a medical device via telemetry interface 518.

Figure 6:
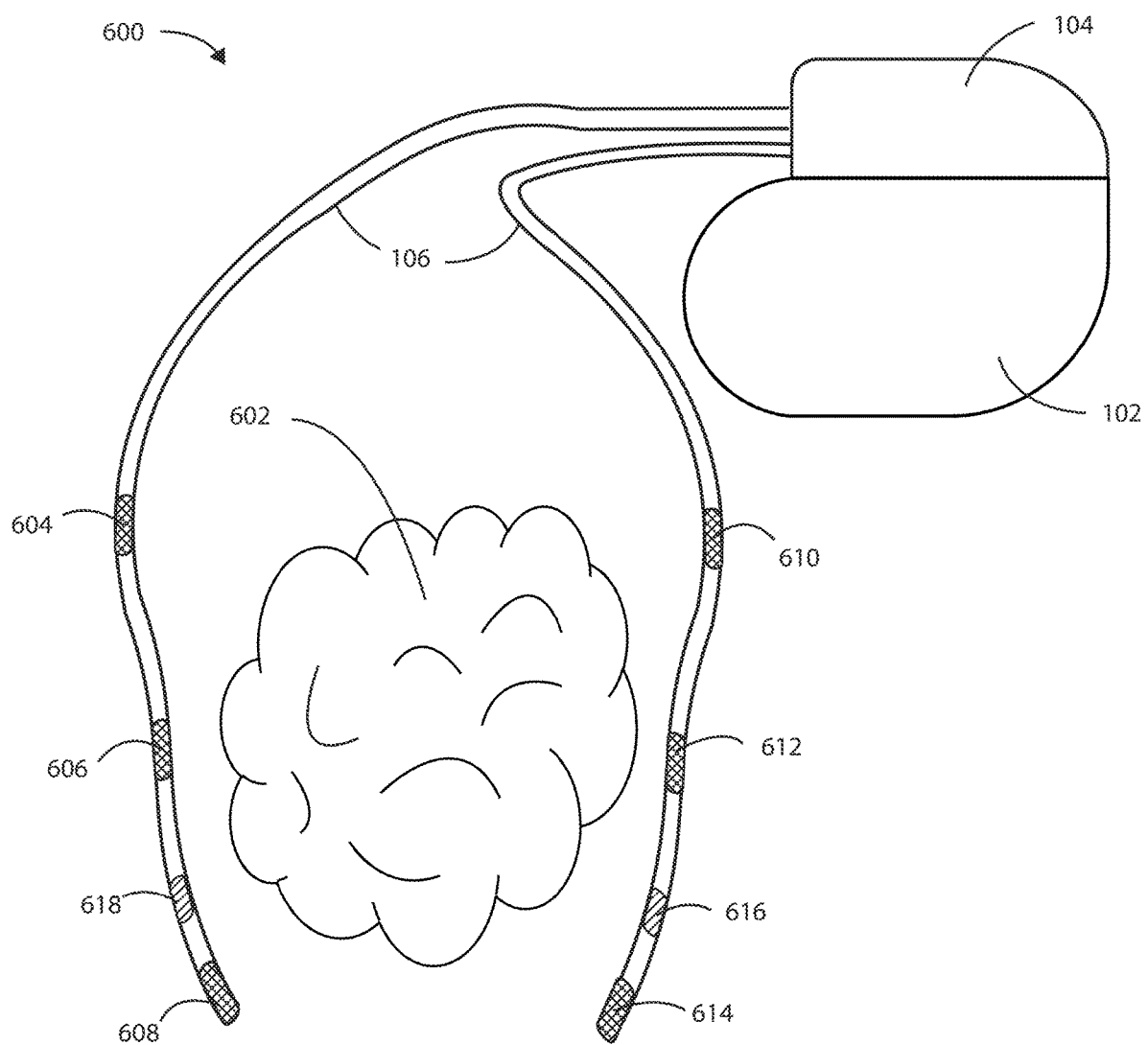
FIG. 6 is a schematic view of a medical device in accordance with various embodiments herein.

Referring now to FIG. 6, a schematic diagram of a medical device 600 is shown in accordance with the embodiments herein. Medical device 600 can include housing 102 and header 104, and one or more leads 106. Leads 106 can include one or more electrodes such as electrodes 604, 606, 608, 610, 612, or 614 disposed along the length of the leads 106. In some embodiments, electrodes 604, 606, 608, 610, 612, or 614 can include electric field generating electrodes and in other embodiments electrodes 604, 606, 608, 610, 612, or 614 can include electric field sensing electrodes. In some embodiments, leads 106 can include both electric field generating and electric field sensing electrodes.

The proximal ends of leads 106 are disposed within the header 104. The distal ends of electrical leads 106 can surround a cancerous tumor 602 such that the electrodes 604, 606, 608, 610, 612, or 614 are brought into proximity of the cancerous tumor 602. In some embodiments, the leads 106 can be positioned within the vasculature such that electrodes 604, 606, 608, 610, 612, or 614 are adjacent to or positioned within the cancerous tumor 602. However, it will be appreciated that leads 106 can be disposed in various places within or around the cancerous tumor 602. In some embodiments, the leads 106 can pass directly through the cancerous tumor 602.

In some embodiments, the leads 106 can include one or more tracking markers 616 or 618 along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be generated between various combinations of electrodes 604, 606, 608, 610, 612, or 614 disposed along leads 106 to create an electric field. For example, one or more electric field vectors can be generated between electrodes 604 and 610. Similarly, one or more electric field vectors can be generated between electrodes 606 and 612. It will also be appreciated that one or more electric field vectors can be generated between any combination of electrodes 604, 606, 608, 610, 612, or 614. In some embodiments, one or more electric field vectors can be generated between any combination of electrodes 604, 606, 608, 610, 612, or 614 and the housing 102 of medical device 400. It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

Referring now to FIGS. 7-11, various embodiments of an electric field shaping element are shown. The electric field shaping elements can be formed from insulative or conductive materials, as will be discussed in more detail below. Electric field shaping elements can be configured to be implanted at or near the site of a cancerous tumor. In some embodiments, the electric field shaping elements described herein can be disposed between a cancerous tumor and an adjacent non-cancerous tissue. In some embodiments, a non-cancerous tissue can be a non-tumor containing organ, bone, or vessel. In some embodiments, the electric field shaping elements can be disposed between an adjacent non-cancerous tissue and one or more electric field generating electrodes.

In some embodiments, the electric field shaping elements can be configured to shield an area from an electric field. In some embodiments, the electric field shaping elements can be configured to redirect an electric field. In some embodiments, the electric field shaping elements can be configured to attenuate an electric field. In some embodiments, the electric field shaping elements can be configured to concentrate an electric field. In some embodiments, the electric field shaping elements can be rigid. In other embodiments, the electric field shaping elements can be flexible so as to provide conformational flexibility to the electric field shaping element. Conformational flexibility can allow the electric field shaping elements described herein to assume an amorphous configuration about or around the cancerous tumor and/or organ of interest.

Figure 7:
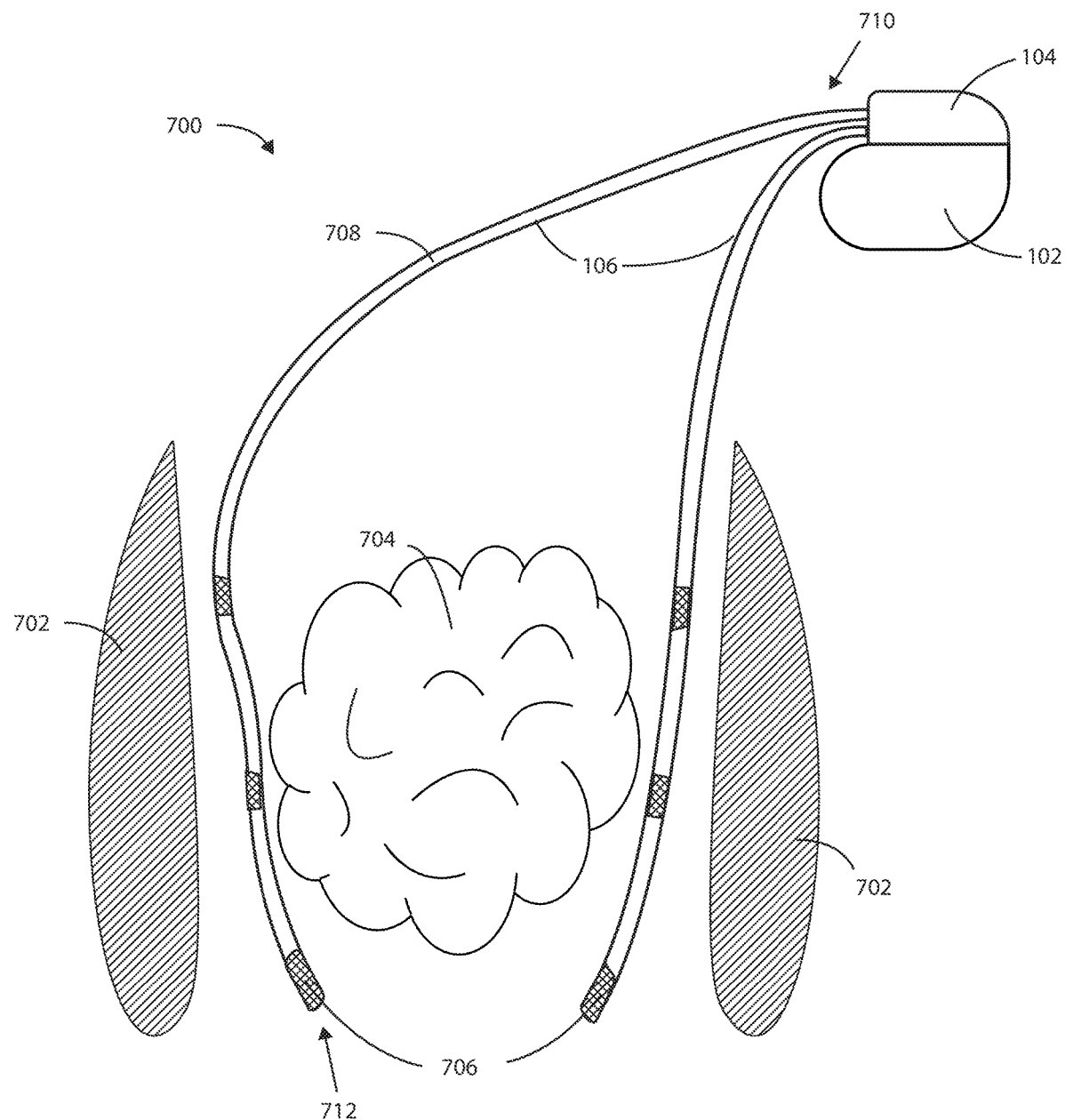
FIG. 7 is a schematic view of a medical device system in accordance with various embodiments herein.

Referring now to FIG. 7, a schematic diagram of medical device system 700 for treating a cancerous tumor 704 is shown in accordance with the embodiments herein. Medical device system 700 can includes a medical device having a housing 102 and a header 104. The medical device system can also include one or more electric field generating electrodes 706 and an electric field shaping element(s) 702 configured to be implanted along with the one or more electric field generating electrodes 706. The electric field shaping element(s) 702 can be formed from a material that alters the spatial area of tissue exposed to the electric field generated by the electric field generating electrodes 706. Leads 106 of medical device system 700 are shown in FIG. 7 positioned at or near a cancerous tumor 704, yet it will be appreciated that tumor 704 may be located within the body such that it is not able to be resected from the organ and/or tissue containing the tumor. As such, it will be appreciated that leads 106 can be positioned within, at, or near the site of a cancerous tumor contained fully or partially within an organ or other bodily tissue.

It will be appreciated that the views shown in FIGS. 7-12 are schematic and that for purposes of ease of illustration the cancerous tumors/tissue therein is generally not shown with surrounding non-cancerous tissue. However, in many cases the cancerous tumors/tissue would actually be directly surrounded by at least some amount of non-cancerous tissue.

In some embodiments, the electric field shaping element (s) can be configured to be physically separated from the lead 106 and the one or more electric field generating electrodes 706. In some embodiments, the electric field shaping element(s) can be configured to be physically connected to the lead 106 and the one or more electric field generating electrodes 706. In some embodiments where the electric field shaping element(s) are configured to be physically connected to the lead 106 and the one or more electric field generating electrodes 706, the electric field shaping element(s) are not in direct electrical contact with electrodes 706. In some embodiments, the housing 102 of the medical device (not shown) can serve as either an electric field generating electrode or an electric field sensing electrode.

The medical device system 700 can also include one or more leads 106. The electric field generating electrodes 706 can be disposed along the length of the lead 106. In some embodiments, the lead can include one or more electric field sensing electrodes disposed along the length of the lead 106. The lead 106 can include a lead body 708 having a proximal end 710 and a distal end 712. The lead body 708 can include one or more conductors (not shown) passing through the lead body 708 and providing electrical communication between the one or more electric field generating electrodes 706 and the proximal end 710 of the lead body 708.

Figure 8:
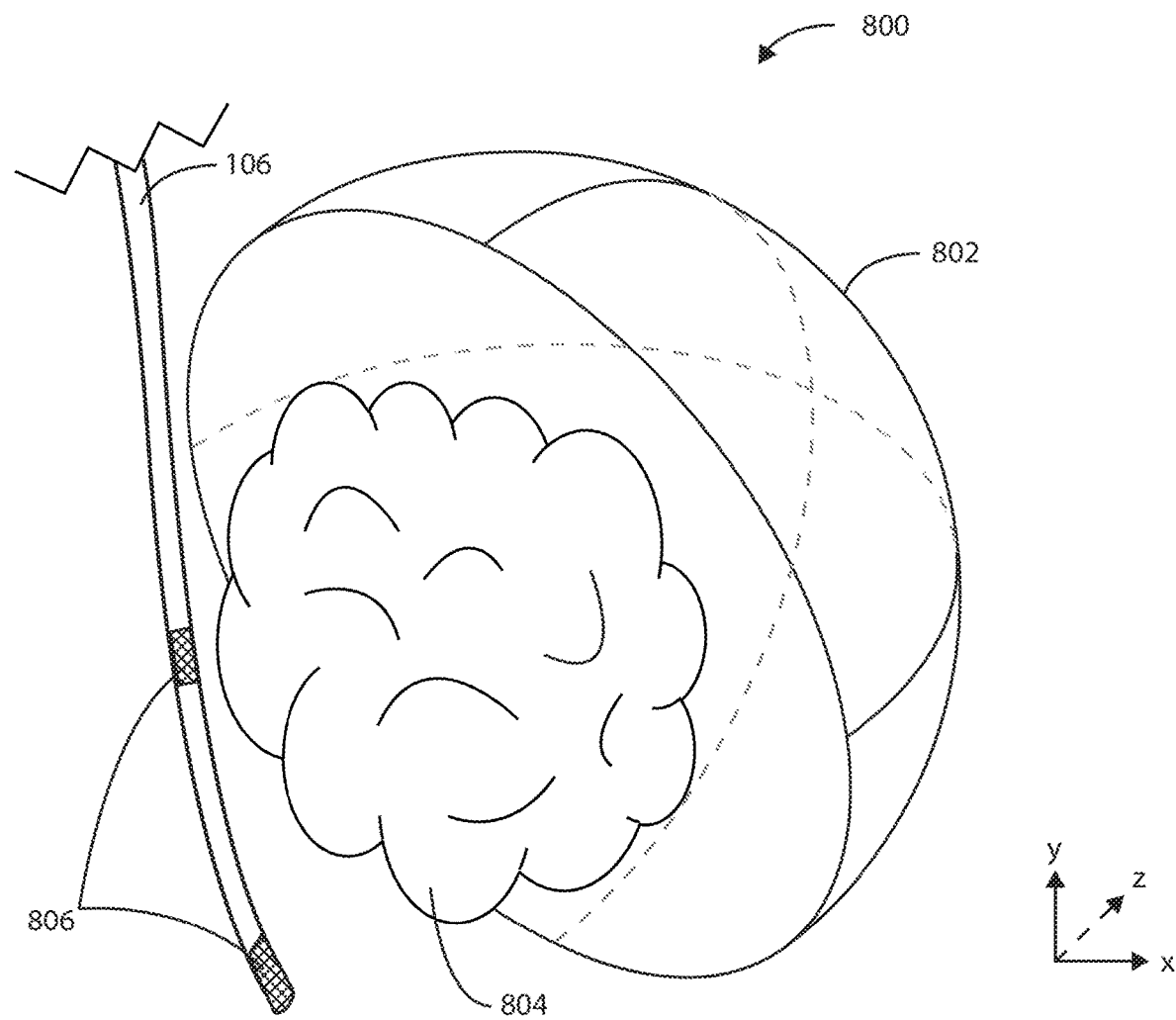
FIG. 8 is a schematic view of a medical device system in accordance with various embodiments herein.

Referring now to FIG. 8, a schematic diagram of a medical device system 800 is shown in accordance with the embodiments herein. Medical device system 800 includes a semi-spherical electric field shaping element 802 configured to enclose a region around a cancerous tumor 804 and to shield non-cancerous tissue from an electric field generated by electrodes 806. Electric field shaping element 802 can be implanted at a site at or near a cancerous tumor 804. Electric field shaping element 802 can surround a majority of the cancerous tumor 804. In some embodiments, electric field shaping element 802 can be formed form a rigid material, and in other embodiments, electric field shaping element 802 can be formed form a flexible material. While electric field shaping element 802 is depicted as a semi-spherical shape, it will be appreciated that this is a non-limiting example and that electric field shaping element 802 can be ovoid, parabolic, rectangular, and the like.

Lead 106 of medical device system 800 is shown in FIG. 8 positioned at or near a cancerous tumor 804, yet it will be appreciated that tumor 804 may be located within the body such that it is not able to be resected from the organ and/or tissue containing the tumor. As such, it will be appreciated that lead 106 can be positioned within, at, or near the site of a cancerous tumor contained fully or partially within an organ or other bodily tissue.

Figure 9:
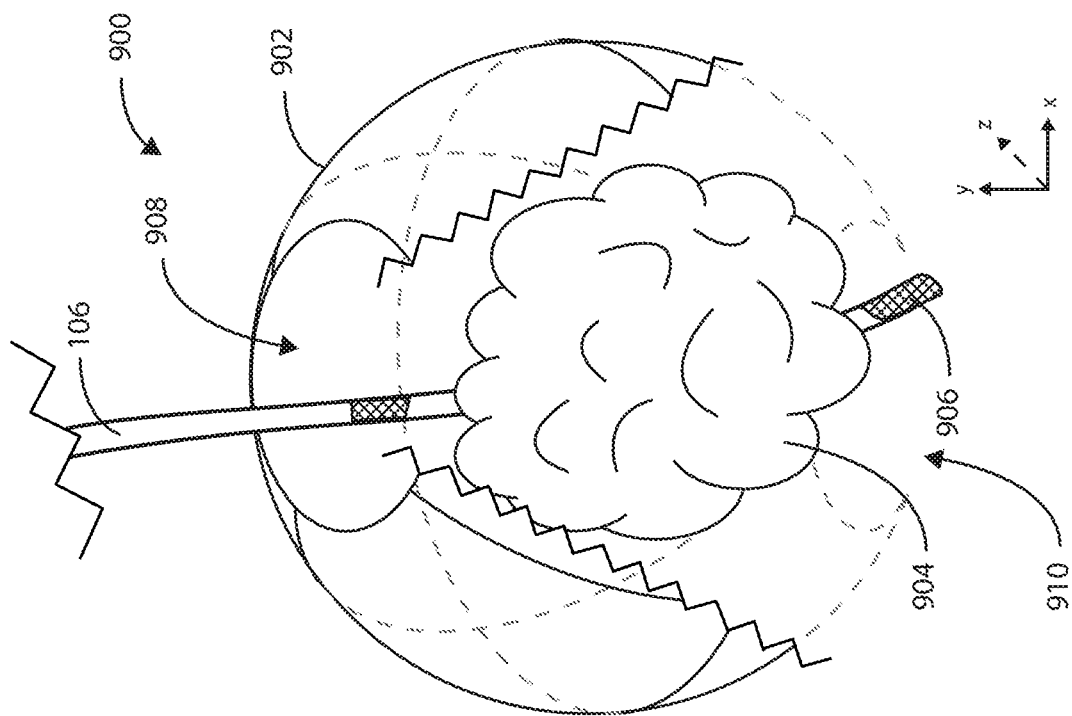
FIG. 9 is a schematic view of a medical device system in accordance with various embodiments herein.

Referring now to FIG. 9, a schematic diagram of a medical device system 900 is shown in accordance with the embodiments herein. Medical device system 900 includes a spherical electric field shaping element 902 configured to enclose a cancerous tumor 904 and to shield non-cancerous tissue from an electric field generated by electrodes 906. Electric field shaping element 902 can be implanted to completely surround a cancerous tumor 904 and act to concentrate the electric field at the site of tumor 904. In some embodiments, electric field shaping element 902 can be configured such that it includes a hinge and closure on opposite sides. In some embodiments, electric field shaping element 902 can be configured as two equal halves that snap together form a sphere that when implanted can be placed entirely around a cancerous tumor 904. In other embodiments, electric field shaping element 902 can be configured to only partially surround cancerous tumor 904.

Electric field shaping element 902 can include one or more openings such as a top opening 908 and a bottom opening 910 to allow for the passage of a lead 106 through the top or bottom openings 908 and/or 910, respectively, and to the site of the cancerous tumor 904. In some embodiments, electric field shaping element 902 can be formed form a rigid material, and in other embodiments, electric field shaping element 902 can be formed form a flexible material. Lead 106 of medical device system 900 is shown in FIG. 9 positioned at or near a cancerous tumor 904, yet it will be appreciated that tumor 904 may be located within the body such that it is not able to be resected from the organ and/or tissue containing the tumor. As such, it will be appreciated that lead 106 can be positioned within, at, or near the site of a cancerous tumor contained fully or partially within an organ or other bodily tissue.

Figure 10:
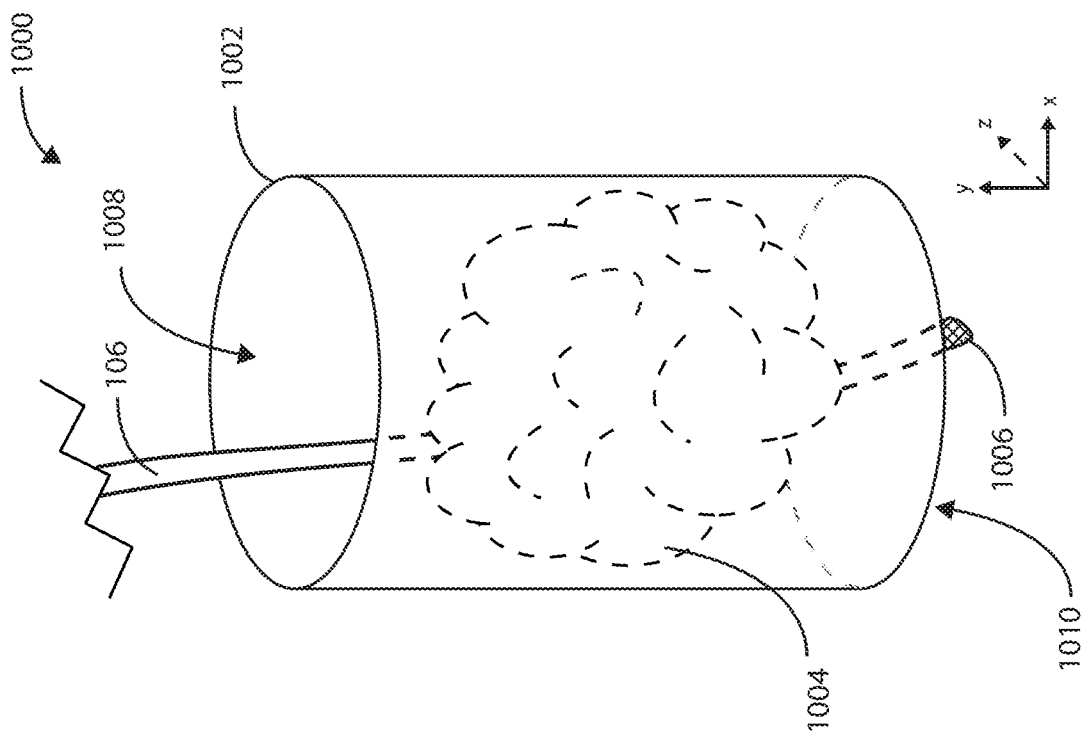
FIG. 10 is a schematic view of a medical device system in accordance with various embodiments herein.

Referring now to FIG. 10, a schematic diagram of a medical device system 1000 is shown in accordance with the embodiments herein. Medical device system 1000 includes a cylindrical electric field shaping element 1002 configured to enclose a cancerous tumor 1004 and to shield non-cancerous tissue from an electric field generated by electrodes 1006. Electric field shaping element 1002 can be implanted to completely surround a cancerous tumor 1004. In some embodiments, electric field shaping element 1002 can be configured such that it includes a hinge and closure on opposite sides so that it can be placed entirely around a cancerous tumor 1004. In some embodiments, electric field shaping element 1002 can be configured as two equal halves that snap together form a cylinder that when implanted can be placed entirely around a cancerous tumor 1004. In other embodiments, electric field shaping element 1002 can be configured to only partially surround cancerous tumor 1004.

Electric field shaping element 1002 can include one or more openings such as a top opening 1008 and a bottom opening 1010 to allow for the passage of a lead 106 through the top or bottom openings 1008 and/or 1010, respectively, and to the site of the cancerous tumor 1004. In some embodiments, electric field shaping element 1002 can be formed form a rigid material, and in other embodiments, electric field shaping element 1002 can be formed from a flexible material. Lead 106 of medical device system 1000 is shown in FIG. 10 positioned at or near a cancerous tumor 1004, yet it will be appreciated that tumor 1004 may be located within the body such that it is not able to be resected from the organ and/or tissue containing the tumor. As such, it will be appreciated that lead 106 can be positioned within, at, or near the site of a cancerous tumor contained fully or partially within an organ or other bodily tissue.

Figure 11:
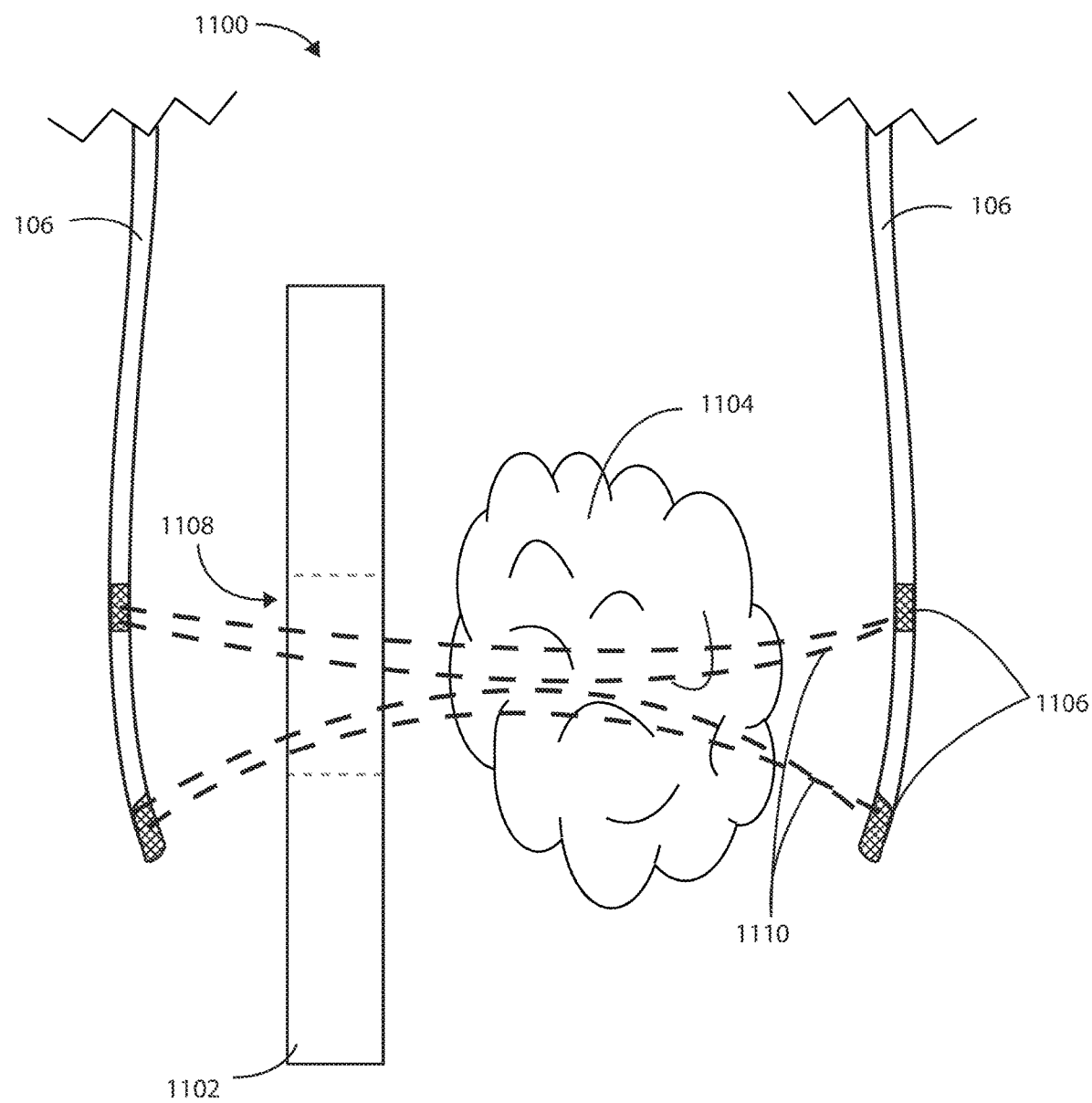
FIG. 11 is a schematic view of a medical device system in accordance with various embodiments herein.

Referring now to FIG. 11, a schematic diagram of a medical device system 1100 is shown in accordance with the embodiments herein. Medical device system 1100 includes a sheet-like electric field shaping element 1102. The sheet-like electric field shaping element 1102 can include one or more apertures 1108 disposed therein to concentrate an electric field generated by electrodes 1106 onto the site of the cancerous tumor 1104. In some embodiments, the sheet-like electric field shaping element 1102 can be made from a polymeric material. In some embodiments, the sheet-like electric field shaping element 1102 can be made from a metallic material. In some embodiments, electric field shaping element 1102 can be formed form a rigid material, and in other embodiments, electric field shaping element 1102 can be formed form a flexible material.

Leads 106 of medical device system 1100 are shown in FIG. 11 positioned at or near a cancerous tumor 1104, yet it will be appreciated that tumor 1104 may be located within the body such that it is not able to be resected from the organ and/or tissue containing the tumor. As such, it will be appreciated that leads 106 can be positioned within, at, or near the site of a cancerous tumor contained fully or partially within an organ or other bodily tissue.

Figure 12:
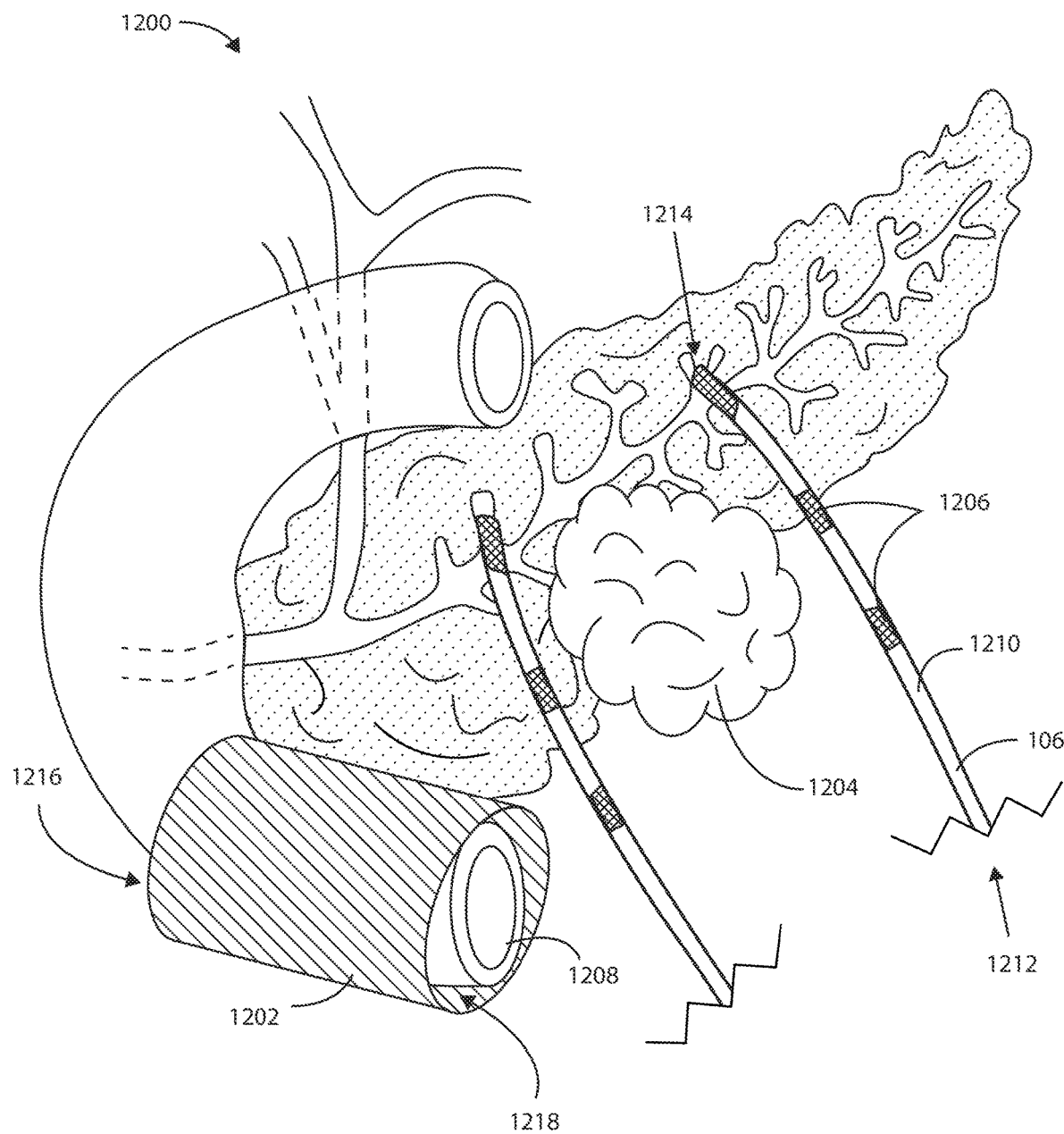
FIG. 12 is a schematic view of a medical device system in accordance with various embodiments herein.

Referring now to FIG. 12, a schematic diagram of a medical device system 1200 for treating a cancerous tumor 1204 is shown in accordance with the embodiments herein (FIG. 12 not to scale). Medical device system 1200 can include one or more electric field generating electrodes 1206 and an electric field shaping element 1202 configured to be implanted along with the one or more field generating electrodes 1206. The electric field shaping element 1202 can be configured to shield a non-cancerous tissue 1208 from an electric field. The electric field shaping element 1202 can be configured to be physically separated from the lead 106 and the one or more electric field generating electrodes 1206. In some embodiments, the housing 102 of the medical device (not shown) can serve as either an electric field generating or an electric field sensing electrode.

The medical device system 1200 can also include one or more leads 106. The electric field generating electrodes 1206 can be disposed along the length of the lead 106. In some embodiments, the lead 106 can include one or more electric field sensing electrodes disposed along the length of the lead 106. The lead 106 can include a lead body 1210 having a proximal end 1212 and a distal end 1214. The lead body 1210 can include one or more conductors (not shown) passing through the lead body 1210 can provide electrical communication between the one or more electric field generating electrodes 1206 and the proximal end 1212 of the lead body 1210.

In some embodiments, electric field shaping element 1202 can be configured to completely surround a non-cancerous tissue, such as tissue 1208. Electric field shaping element 1202 can act to redirect the electric field at the surface of electric field shaping element 1202. In some embodiments, electric field shaping element 1202 can be configured such that it includes a hinge and closure on opposite sides so that it can be placed entirely around non-cancerous tissue 1208. In some embodiments, electric field shaping element 1202 can be configured as two equal halves that snap together form a cylinder that when implanted can be placed entirely around non-cancerous tissue 1208. Electric field shaping element 1202 can include one or more openings such as a top opening 1216 and a bottom opening 1218. In some embodiments, electric field shaping element 1202 can be formed form a rigid material, and in other embodiments, electric field shaping element 1202 can be formed form a flexible material.

In some embodiments, electric field shaping element 1202 can be formed from a contiguous polymeric or contiguous metallic sheet. In some embodiments, the contiguous metal sheet can include one or more apertures disposed therein. The contiguous metal sheet can be configured to effectively shunt an electric field at an exterior surface of the metal sheet and around the non-cancerous tissue to prevent the electric field from contacting the non-cancerous tissue. A polymeric sheet can similarly attenuate an electric field so that the non-cancerous tissue experiences little to negligible electric field. In some embodiments, the contiguous metal sheet or contiguous polymeric sheet can be formed as an expandable lattice.

Leads 106 of medical device system 1200 are shown in FIG. 12 positioned at or near a cancerous tumor 1204, yet it will be appreciated that tumor 1204 may be located within the body such that it is not able to be resected from the organ and/or tissue containing the tumor. As such, it will be appreciated that leads 106 can be positioned within, at, or near the site of a cancerous tumor contained fully or partially within an organ or other bodily tissue.

Figure 13:
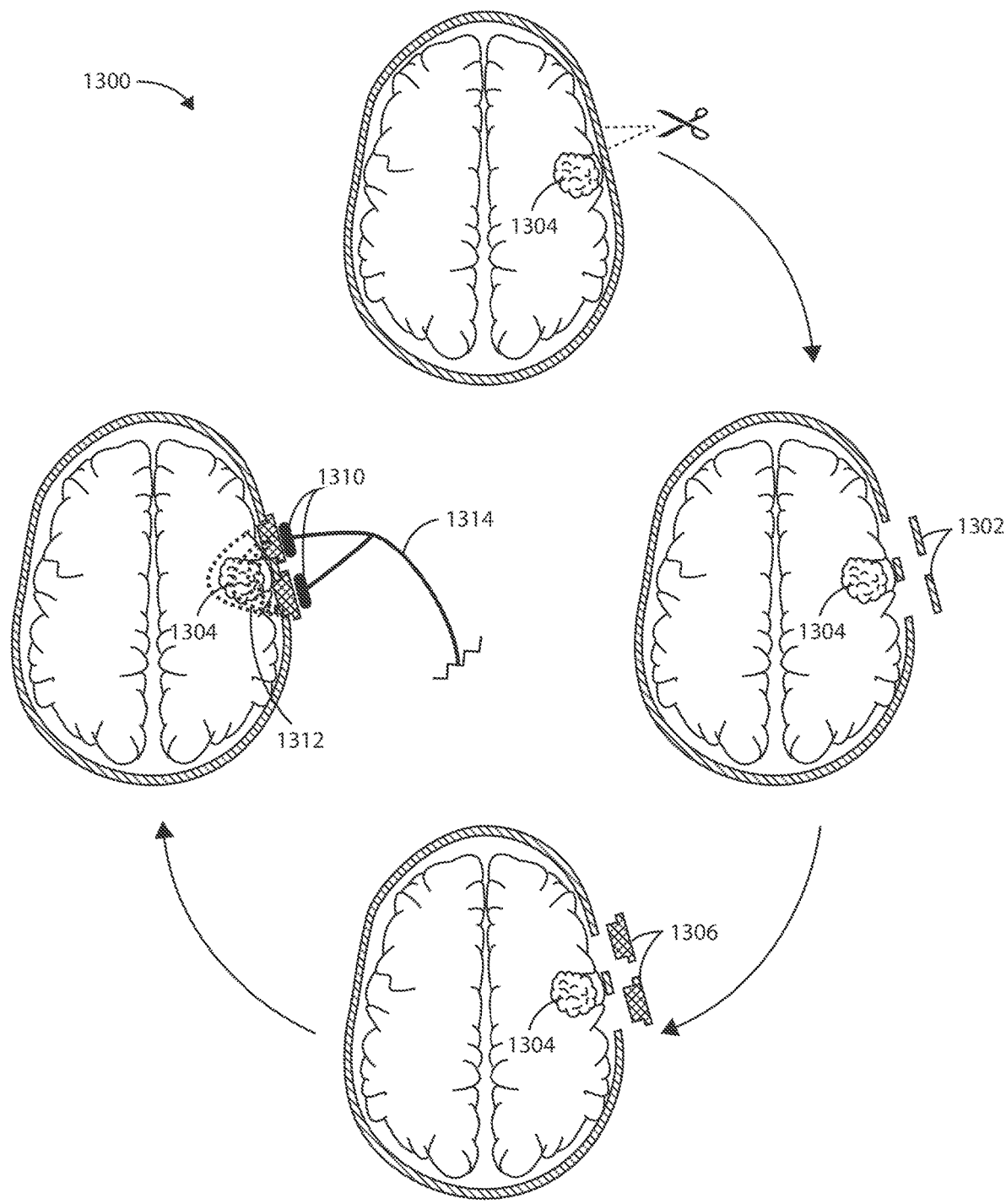
FIG. 13 is a schematic view of a method of treating a cancerous tumor in accordance with various embodiments herein.

Referring now to FIG. 13, a schematic diagram for a method 1300 of treating a cancerous tumor is shown in accordance with the embodiments herein. Method 1300 can include removal of one or more portions 1302 of a patient tissue proximal to a cancerous tumor 1304. The removed portion (s) 1302 of a patient tissue 1302 can include a portion of patient tissue on an outer surface of the body, such as the skull and associated skin and tissue, or it can be a portion of patient tissue found inside of a patient's body, such as connective tissue, fat, or a portion of a diseased organ, bone, or vessel, and the like. Removal of a portion of a patient tissue can facilitate the propagation of an electric field applied from external electrodes because many human tissues (e.g., bone and fat) have low permittivity and conductance and thus break down an electric field before it can reach the target cancerous tumor. Replacement of the removed patient tissue with an electric field shaping element that can increase permittivity and conductance at or near the site of a cancerous tumor can enhance treatment efficacy and reduce energy usage.

It will be appreciated that while FIG. 13 shows removal of one or more portions of a patient tissue, the methods described herein can include scenarios where no patient tissue is removed. For example, in some embodiments, electric field generating leads can be positioned at, near, or within a cancerous tumor, while an electric field shaping element can be delivered to the site of the tumor through transvascular or tunneling techniques. In some embodiments, the electric field shaping elements can be delivered to the site of a cancerous tumor through natural body orifices such as the trachea, bronchial tubes, blood vessels, and the like. The electric field shaping element can be configured to redirect an electric field at the site of a cancerous tumor. In some embodiments, the electric field shaping element can be configured to shield a non-cancerous tissue from an electric field. In some embodiments, the electric field shaping element delivered to the site of a cancerous tumor can be in the form of an amorphous solution material. In some embodiments, the solution material can be a conductive polymeric solution. In other embodiments, the electric field shaping element delivered to the site of a cancerous tumor can be in the form of a metallic stent or sheet.

Method 1300 can include replacing a segment of a patient tissue 1302 proximal to a cancerous tumor 1304 with a material 1306 that attenuates an electrical field less than the patient tissue being replaced. In some embodiments, the method 1300 can include replacing the patient tissue 1302 with a natural material. In some embodiments, the method 1300 can include replacing the patient tissue 1302 with a synthetic material. The method 1300 can also include placing one or more externally coupled electrodes 1310 on the opposite side of the material 1306 that has replaced the patient tissue 1302 and generating an electric field 1312 at the site of the cancerous tumor 1304 from the one or more electrodes 1310. In some embodiments, the method 1300 can include generating an electric field 1312 at the site of the cancerous tumor 1304 by using an externally coupled electrodes 1310 disposed on lead 1314 and in electrical communication with an electric field generator (not shown) disposed on the exterior of the patient's body. In some embodiments, material 1306 can serve as two or more electrodes and can be used to generate an electric field 1312 at the site of the cancerous tumor 1304.

Figure 14:
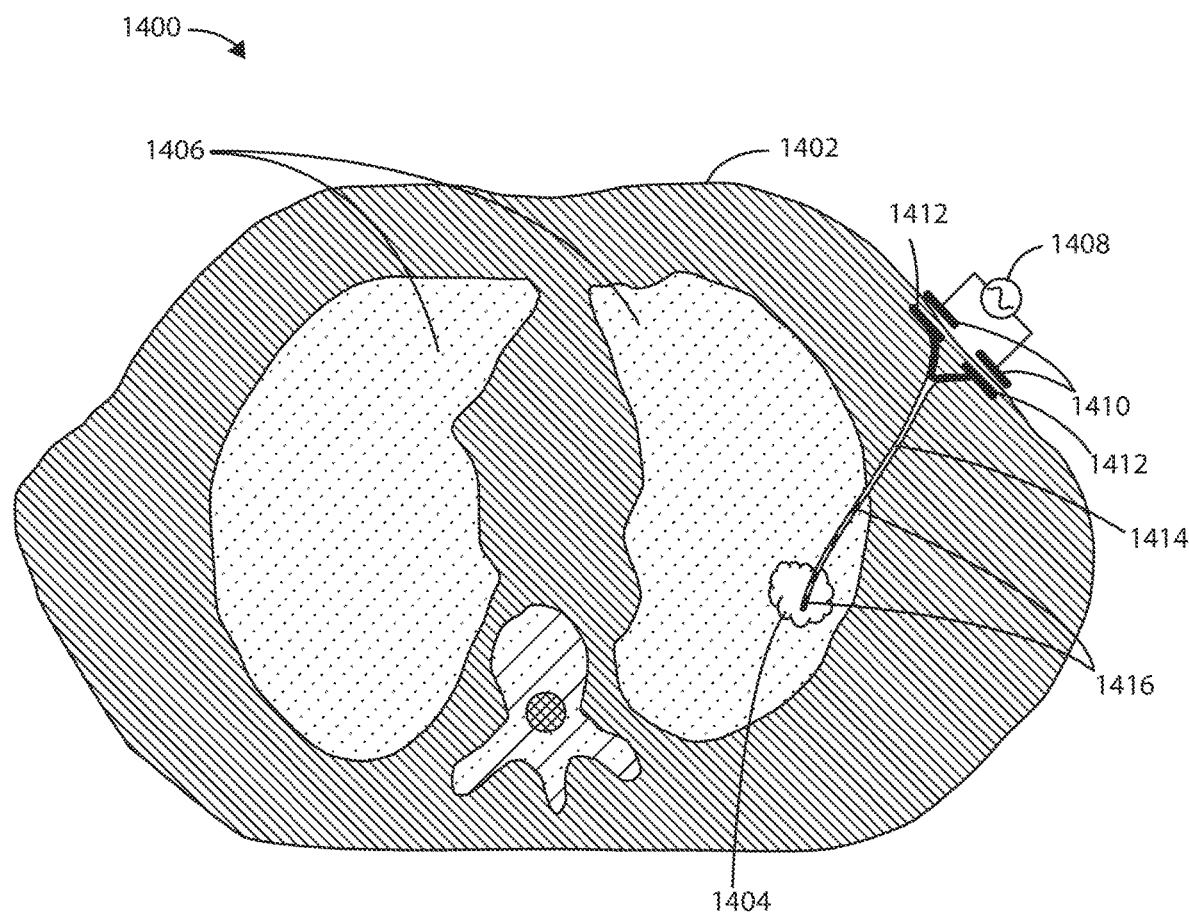
FIG. 14 is cross-sectional view of a human body in accordance with various embodiments herein.

Referring now to FIG. 14, a schematic diagram of a cross-sectional view 1400 of a human thorax 1402 is shown. The cross sectional view 1400 of the human thorax 1402 includes the lungs 1406. A cancerous tumor 1404 is shown disposed within the lung tissue 1406. An external electric field generating system 1408, including external surface electrodes 1410 (or external surface coupling structures), can be disposed external to the thoracic cavity, while an internal lead 1414 can be implanted entirely within the body. In some embodiments, the internal lead 1414 can be partially implanted within the body and partially external to the body. It will be appreciated that while only one lead 1414 is shown, one or more leads can be included.

The proximal portion of lead 1414 can include internal surface electrodes 1412 (or internal surface coupling structures) that can be disposed internally next to the internal surface of the skin, while the distal portion of the lead can be disposed at, near, or within a cancerous tumor 1404, deep inside the thorax. The external surface electrodes 1410 or coupling structures and internal surface electrodes 1412 or coupling structures can be coupled, such as wirelessly coupled, to bring an electric field to the site of a cancerous tumor within the body via lead 1414. The external surface electrodes 1410 and internal surface electrodes 1412 can be coupled using various mechanisms, such as, but not limited to capacitive coupling, inductive coupling, conductive coupling, and radio frequency and acoustic energy transfer techniques, and the like.

Lead 1414 can include one or more electric field generating electrodes 1416 disposed at, near, or within a cancerous tumor so as to create a direct electric field at the site of the cancerous tumor. It will be appreciated that an external electric field generating system 1408 can be configured to be coupled to the one or more implanted electric field generating electrodes to deliver an electric field to the site of the cancerous tumor. Such a configuration can provide a direct electric field at the site of the cancerous while bypassing any interference due to the presence of fat, muscle, bone, and the like. Lead 1414 can be delivered to the site of a cancerous tumor through natural body orifices such as the trachea, bronchial tubes, blood vessels, and the like. In some embodiments, lead 1414 can be surgically delivered to the site of a cancerous tumor. In some embodiments, an electric field shaping element (not shown) can be implanted along with lead 1414 at the site of a cancerous tumor. In some embodiments, an electric field shaping element can be delivered through a natural body orifice as described above.

It will be appreciated that direct delivery of an electric field to the site of a cancerous tumor 1404 using one or more leads 1414 can require less energy than initiating an electric field at the skin surface. In addition, this type of combination internal/external configuration can eliminate the need for an implanted battery, thus prolonging the useful life of the implanted components of the system. This type of passive yet active implantable system allows for therapy energy to be provided through the skin. In comparison to purely external approaches, it allows for an efficient implanted pathway for the therapy energy to follow, instead of inefficiently driving such energy through fat, bone, etc. Also, creating a therapeutic electric field directly at the site of a cancerous tumor can also lessen side effect of tissue heating at the exterior surface of the body.

Figure 15:
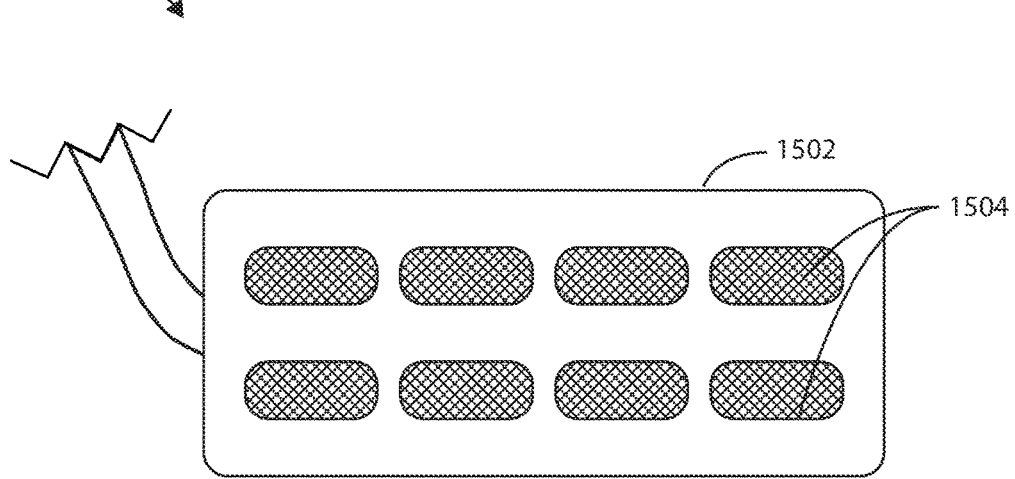
FIG. 15 is a schematic view of a lead in accordance with various embodiments herein.

Referring now to FIG. 15, an exemplary portion 1500 of a lead for internal or external use is shown in accordance with the embodiments herein. The portion 1500 includes a patch device 1502 or coupling device having multiple electrodes or energy transmitting or receiving elements 1504 disposed thereon. The multiple electrodes or energy transmitting or receiving elements can include various elements for the wireless transmission or reception of electrical energy including, but not limited to, wire coils, wire loops, antennas, and the like. Wireless energy transmission can proceed via various mechanisms, including, but not limited to capacitive coupling, inductive coupling, conductive coupling, and radio frequency and acoustic energy transfer techniques, and the like In some embodiments, one or more patch devices can be utilized to deliver an electric field to the site of a tumor within the body. For example, in the example shown in FIG. 14, a patch device can be disposed external to the thoracic cavity and can be electrically connected to an external electric field generating system 1408. A similar patch device can be disposed internally next to the internal surface of the skin. In such a configuration, the external patch device and internal patch device can be wirelessly coupled to one another and to one or more implanted leads having one or more electric field generating electrodes disposed thereon. Patch device 1502 can be configured to couple one or more leads to multiple implanted electrodes at the site of a cancerous tumor within the body.

Electric Field Shaping Elements

The medical device systems described herein can include various combinations of leads, electrodes, and electric field shaping elements. Electric field shaping elements can be implanted at or near the site of a tumor in conjunction with a medical device, which can generate an electric field at the site of the tumor. In some embodiments, the electric field shaping elements can be implanted along with the entire medical device, inclusive of the leads, electrodes, and electric field generator hardware. In some embodiments, the electric field shaping elements can be implanted along with one or more portions of the medical device, such as the leads, electrodes, and/or electric field generator hardware. In other embodiments, the electric field shaping elements can be implanted along with one or more leads and electrodes at or near the site of the cancerous tumor, and the electric field generator hardware can be externally positioned outside the body such that it is electrically coupled to the internal lead and electrode components. Electrically coupling the external hardware to internal lead and electrode components can include various mechanisms, such as, but not limited to capacitive coupling, inductive coupling, conductive coupling, and radio frequency and acoustic energy transfer techniques, and the like.

Electric field shaping elements can be formed from high-dielectric polymeric or metallic materials having either insulative or conductive properties. Biocompatible insulating materials can include, but not be limited to materials such as polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, tantalum pentoxide, other high capacitance oxides, or derivatives of any of the foregoing. In other embodiments, the insulative materials can be organic materials such as ceramics, quartz, or glass.

Biocompatible conductive materials can include, but not be limited to polymeric materials such as polypyrrole, polyaniline, poly(3,4-ethylenedioxythiophene), polythiophene, polythiophene-vinylene, poly(2,5-thienylenevinylene), poly(3-alkylthiophene, poly(p-phenylene), poly-p-phenylene-sulphide, poly(p-phenylenevinylene), poly(p-phenylene-terephthalamide), polyacetylene, poly(isothianaphthene), poly(α-naphthylamine), polyazulene, polyfuran, polyisoprene, polybutadiene, poly(3-octylthiophnene-3-methylthiophene), poly(p-phenylene-terephthalamide), and derivatives thereof. Biocompatible conductive materials can also include, but not be limited to, metallic materials such as palladium, platinum, gold, nitinol, nickel-cobalt alloys such as MP35N®, various alloys including stainless steel, and the like.

Electric field shaping elements suitable for use herein can be shaped into many 3-dimensional configurations. In some embodiments, the electric field shaping elements can be configured into the form of a sphere, a cylinder, a convex disc, a concave disc, a flat disc, a rectangle, a square, a parabola, and the like. The electric field shaping elements can be rigid or flexible. In some embodiments, the electric field shaping elements can be modular such that they include one or more pieces that can be connected together at the site of a cancerous tumor via a hinge or snap mechanism, or by a suture mechanism. Many different techniques and structures can be used for to connect the one or more pieces and so embodiments herein are not limited to any particular structure. In some embodiments, the electric field shaping elements can be modular such that they include one or more pieces that are not connected to one another. In some embodiments, the electric field shaping elements can include areas that are contiguous and areas that are not contiguous such that a portion of an organ or vessel can pass through a section of the electric field shaping element. In some embodiments, the electric field shaping elements can be rigid. In some embodiments, the electric field shaping elements can be flexible so as to provide conformational flexibility to the electric field shaping element. Conformational flexibility can allow the electric field shaping elements described herein to assume an amorphous configuration about or around the cancerous tumor and/or organ of interest.

In some embodiments, the electric field shaping elements can be a sheet. In some embodiments, the electric field shaping element can include a rigid sheet. In some embodiments, the electric field shaping element can include a flexible sheet. It will be appreciated that a flexible sheet can take the form of the underlying organ or cancerous tumor upon which it is positioned. It will be appreciated that in some embodiments, a flexible sheet can take the form of the underlying non-cancerous organ tissue upon which it is positioned. In some embodiments, an electric field shaping element in the form of a sheet can include one or more apertures disposed thereon. In other embodiments, the electric field shaping element can assume an amorphous shape.

Electric field shaping elements can also be configured to break down an electric field at or near the site of a cancerous tumor to reduce exposure of non-cancerous tissues to electric fields. The electric field shaping elements can take on the form of a contiguous device having a hollow interior surrounded by a sheet, a mesh, or a netting that is configured to block, or shield, one or more non-cancerous tissues from a generated electric field. The contiguous device having a hollow interior can be open at one or more sections of the device. The contiguous device can be modular such that it includes one or more pieces that can be connected together at the site of a cancerous tumor, such as by a hinge or snap mechanism, or by a suture mechanism. When configured as a contiguous device having a hollow interior, an electric field shaping element can act as a Faraday cage.

Without being bound by a particular theory, it is believed that a Faraday cage acts to shunt a local electric field to the exterior surface of the cage so that it does not penetrate the inside of the cage. Electric charges within the cage can move throughout the conductive material of a contiguous device to cancel the effects of the electric field so that they do not propagate into the interior of the cage. A Faraday cage can be placed around non-cancerous tissues to effectively shunt the electric field at the cage exterior and prevent the electric field from contacting the non-cancerous tissues. In some embodiments, the non-cancerous tissue can be a non-tumor containing organ, bone, or vessel. In some embodiments, one or more electric field shaping elements can be configured at or near the site of a cancerous tumor to act as a Faraday cage to surround one or more non-cancerous tissues.

Leads and Electrodes

The leads described herein can be placed into the body near the site of a cancerous tumor using a number of techniques. Placement of one or more leads can include using techniques such as transvascular placement, tunneling into the subcutaneous space, and/or surgical placement. In some embodiments, the placement of one or more leads can include placement via one or more natural body orifices. The leads can be placed adjacent to or within a cancerous tumor. In some embodiments, multiple leads can be used near to or far from the cancerous tumor.

In some embodiments one or more leads described herein can be placed in the subcutaneous space. Electrodes on leads placed in the subcutaneous space can be used as the primary near-field generating electrode or as a far-field field generating electrode. In some embodiments, electrodes on leads placed in the subcutaneous space can be used as the primary near-field generating electrode or as a far-field field generating electrode in conjunction with the housing of a medical device. Likewise, one or more leads can be placed transvascularly to act as far-field field generating electrodes in conjunction with an electrode at or near the site of the cancerous tumor or in conjunction with the housing of a medical device.

The leads and electrodes described herein can include additional functional and structural features. In some embodiments, the leads can include those that are compatible with imaging and treatment techniques, including but not limited to MRI (magnetic resonance imaging), X-ray imaging, deep brain stimulation techniques, and/or radiation therapy. In some embodiments, the leads can include one or more conductor cores made from conducting materials. The conductor cores can be formed from conducting materials including metals and/or other conducting materials. Metals can include, but are not limited to, palladium, platinum, silver, gold, copper, aluminum, various alloys including stainless steel, nickel-cobalt alloys such as MP35N® and the like. In some embodiments, the conductor core can be a multifilar coil, including but not limited to a bifilar coil, a trifilar coil, and a quadfilar coil.

In some embodiments, electrodes can be disposed along the length of one or more leads as described herein. Suitable materials for use in the electrodes described herein can include metals such as palladium, to minimize coupling and artifact generation in magnetic fields. In some embodiments, electrodes can be made from other metals and/or other conducting materials. Metals can include, but are not limited to, palladium, platinum, platinum alloys such as platinum-iridium alloy, gold, copper, tantalum, titanium, various alloys including stainless steel, and the like. In some embodiments, electrodes can be in the form of wound coils that can provide an added benefit of increased surface area without compromising flexibility of the electrodes. In some embodiments, the implantable device housing can serve as an electrode.

The leads described herein can also include one or more electrodes disposed along the length of the lead. The leads can include two or more electrodes disposed along the length of the lead. In some embodiments, the electrodes can be tip electrodes found at the distal end of the lead. In other embodiments, the electrodes can be ring electrodes found along the lead but not at the tip of the lead. In some embodiments, the electrodes can be coil electrodes. In some embodiments, a ring or tip electrode can be positioned in or adjacent to a tumor or cancerous tissue and a coil electrode can be positioned farther from the tumor or cancerous tissue in order to help provide spatial diversity to the generated electric fields. In some embodiments, one or more electrodes can have a length along the lengthwise axis (e.g., proximal to distal axis) of about 0.5, 1, 1.5, 2, 3, 4, 5, 7.5, 10, 15, 20, 30, 40, 50, 75, 100 mm or more. In some embodiments, one or more of the electrodes can have a length falling within a range wherein any of the foregoing distances can serve as the upper or lower bound of the range, provided that the upper bound is greater than the lower bound.

The leads can be unipolar, bipolar, or multipolar. In some embodiments, a unipolar lead can include a lead that generates an electric field between one electrode and the housing of the medical device. In some embodiments, a bipolar lead can include a lead that can generate and electric field between two electrodes disposed along the lead, or between both electrodes and the housing of the medical device. In some embodiments, a multipolar lead can include a lead that can generate an electric field between the more than two electrodes disposed along the lead, between more than two electrodes and the housing of the medical device, or any number of combinations of configurations of electrodes and the housing of the medical device.

The electrodes suitable for use here can be made of conductive polymers such as carbon filled silicone, polyacetylene, polypyrrole, polyaniline, polythiophene, polyfuran, polyisoprene, polybutadiene, polyparaphenylene, and the like. In other embodiments, the electrodes can be insulated. In some embodiments, the insulation surrounding and electrode can include microporous insulators to prevent cellular apposition, yet still allow for current flow. Microporous insulators can be made from a number of the insulating materials described herein, including but not limited to polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, or derivatives thereof. In some embodiments, the electrodes can be coated with various materials, including but not limited to hydrogels or fractal coatings such as iridium oxide, titanium oxide, tantalum pentoxide, other metal oxides, poly(p-xylylene) polymers such as Parylene, and the like.

A number of lead fixation techniques and configurations can be used in accordance with the embodiments herein. Some non-limiting examples of lead fixation techniques can include biocompatible glue fixation, talon fixation, helix coil fixation, passive centering of the lead in the vascular system, tine fixation within the localized vascular system, spiral bias fixation within the localized vascular system, compression fixation, suture sleeve fixation, and the like. In some examples, the leads embodied herein can be placed within the vascular system surrounding or adjacent to the site of the cancerous tumor. In other embodiments, the leads embodied herein can be place surgically at or within or surrounding the site of the cancerous tumor.

The leads suitable for use herein can also include one or more open lumens that run the entire longitudinal length of, or a select portion of the longitudinal length of the lead. In some embodiments, the open lumen can include an integrated biopsy apparatus suitable for obtaining biopsy samples from a cancerous tumor site on a periodic basis to monitor disease progression and/or regression. Leads having an open lumen can also be configured to include an integrated drug delivery lumen that can deliver one or more drugs, such as steroids or chemotherapy agents, to the site of the tumor in a single bolus or periodically via a metered pump. The leads can include one or more portals disposed along the length of the lead to provide an outlet for drug delivery at or near the site of a cancerous tumor.

In some embodiments a portion of the lead or the entire lead can include a drug eluting coating. In some embodiments, the drug eluting coating can include an anti-inflammatory agent, such as a steroid. In some embodiments, the steroid can be dexamethasone. In other embodiments, the drug eluting coating can include a chemotherapy agent. In some embodiments, the chemotherapy agent can include a taxane or derivatives thereof, including but not limited to paclitaxel, docetaxel, and the like. In other embodiments, the drug eluting coating can be configured to release additional classes of chemotherapy agents, including, but not limited to alkylating agents, plant alkaloids such as *vinca* alkaloids, cytotoxic antibiotics, topoisomerase inhibitors, and the like. In some embodiments, the drug eluting coating can be configured to release the drug from the coating in a time-release fashion.

The leads herein can adopt a number of shapes or configurations. In some embodiments, the leads can be linear and in other embodiments the leads can be circular. A circular lead may be a completely closed loop or it may be a semi-closed loop. In some embodiments, the lead can include a bendable core that can allow the lead to be shaped into many configurations, including but not limited to a U shape, an S shape, a spiral shape, a half circle, an oval, and the like.

In yet other examples, the leads suitable for use herein can include fluorimetric or magnetic markers that can assist the clinician in precise placement at or near the site of a cancerous tumor. The leads can also include integrated pH sensors for detecting the change in the pH at or near the cancerous tumor or other chemical sensors suitable for analyzing the concentration of a chemical analyte of interest.

Therapy Parameters

Successful treatment of cancerous tumors can depend on a number of variables, including electric field strength, frequency, cell heterogeneity, cell size, cancer cell type, tumor size, and location within the body. A variety of therapy parameters can be implemented using the medical devices described herein. One or more therapeutic parameter sets can be programmed into the memory of the medical devices and implemented by the control circuitry 306, shown in FIG. 3. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective spinning electric field; modulating a voltage control mode or a current control mode; implementing one or more duty cycles; pulse width modulation; manipulation of the waveform shape and/or pulse sequence; and the occasional use of high frequency or high electric fields strength pulses.

The therapeutic parameter sets can be programmed into a medical device to operate autonomously, or they can be queried and manipulated by the patient or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit 320. In some embodiments, one or more therapeutic parameter sets can be implemented simultaneously. In other embodiments, one or more therapeutic parameter sets can be implemented in an alternating fashion.

Figure 16:
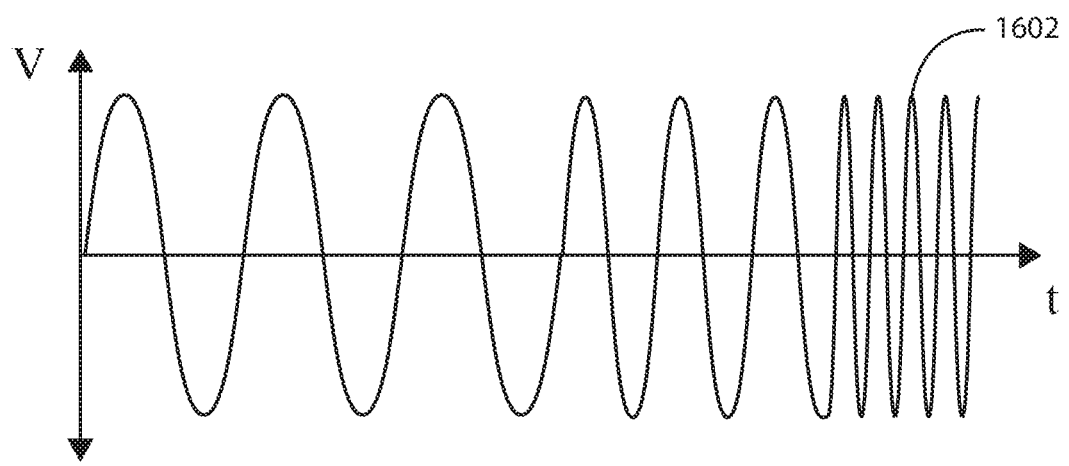
FIG. 16 is a plot of an exemplary therapy parameter in accordance with various embodiments herein.

Referring now to FIG. 16, exemplary plot 1602 shows an example of sweeping through a range of frequencies at the site of a cancerous tumor. Plot 1602 shows an alternating electric field, where the frequency is increased over time as the therapy is applied to the cancerous tumor. In some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy.

Electric Field Generators

The medical devices embodied herein can include electric field generators particularly suited for therapeutic and diagnostic techniques used during the course of treatment for a cancerous tumor. In some embodiments, the electric field generators suitable for use herein can include those that have been treated by radiation hardening to make the components resistant to the damaging effects of radiation therapy treatments often prescribed as a main line treatment for cancerous tumors. Electric field generators can include components such as those described in reference to FIGS. 3 and 5 above.

Electric field generators embodied herein can be programmed with any number of therapeutic parameter sets as described. The electric field generators can be programmed prior to implant, or they can be programmed by a clinician using an external computation device such as a programmer, a home-based unit, and/or a mobile unit (e.g. a cellular phone, personal computer, smart phone, tablet computer, and the like). In some embodiments, therapy parameters can be delivered to the electric field generator via a telemetry circuit. In some embodiments, the electric field generator can include a recharge circuit communicatively coupled to a receiver coil to facilitate transcutaneous recharging of the medical device. In some embodiments, the electric field generator can communicate wirelessly between the receiver coil and an external charging device.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A medical device system for treating a cancerous tumor comprising:
   at least two leads each having one or more implantable electric field generating electrodes disposed along a length of each lead; and
   an electric field shaping element configured to be implanted along with the at least two leads having one or more electric field generating electrodes, the electric field shaping element comprising a material that alters the spatial area of tissue exposed to an electric field;
   wherein the electric field shaping element is physically separate from the leads and the electric field generating electrodes;
   wherein the electric field shaping element is in the form of a flat disc, a rectangle, or a square, and is configured to be placed near the cancerous tumor; and
   wherein the electric field shaping element comprises one or more apertures disposed therein to concentrate an electric field onto a cancerous tumor.

2. The medical device system of claim 1, each lead comprising a lead body having a proximal end and a distal end, the lead body comprising one or more conductors passing through the lead body and providing electrical communication between the one or more electric field generating electrodes and the proximal end of the lead body.

3. The medical device system of claim 1, the electric field shaping element comprising a material that shields an electrical field.

4. The medical device system of claim 1, the electric field shaping element configured to be positioned between a cancerous tumor and an adjacent non-cancerous tissue or between an adjacent non-cancerous tissue and the one or more electric field generating electrodes.

5. The medical device system of claim 1, the electric field shaping element comprising a material that redirects an electrical field.

6. The medical device system of claim 1, the electric field shaping element comprising a material that attenuates the energy of an electrical field.

7. The medical device system of claim 1, the electric field shaping element comprising a high-dielectric material.

8. The medical device system of claim 1, the electric field shaping element comprising at least one of
   a concave shape with respect to the cancerous tumor; and
   a parabolic shape with respect to the cancerous tumor.

9. The medical device system of claim 1, the electric field shaping element comprising a polymer sheet.

10. The medical device system of claim 1, the electric field shaping element comprising a metal sheet.

11. A medical device system for treating a cancerous tumor comprising:
    at least two leads each having one or more implantable electric field generating electrodes disposed along a length of each lead; and
    an electric field shaping element configured to be implanted along with the at least two leads having one or more field generating electrodes, the electric field shaping element configured to shield a non-cancerous tissue from an electric field;
    wherein the electric field shaping element is physically separate from the leads and the electric field generating electrodes;
    wherein the electric field shaping element is in the form of a flat disc, a rectangle, or a square, and is configured to be placed near the cancerous tumor; and
    wherein the electric field shaping element comprises one or more apertures disposed therein to concentrate an electric field onto a cancerous tumor.

12. The medical device system of claim 11, the electric field shaping element comprising a material that redirects an electrical field.

13. The medical device system of claim 11, the electric field shaping element comprising a contiguous metal sheet, the contiguous metal sheet comprising one or more apertures disposed therein to effectively shunt an electric field at an exterior surface of the metal sheet to prevent the electric field from contacting the non-cancerous tissue.

14. The medical device system of claim 11, the electric field shaping element comprising an expandable lattice.

* * * * *